US008247020B2

(12) United States Patent  (10) Patent No.: US 8,247,020 B2
Sims et al.  (45) Date of Patent: *Aug. 21, 2012

(54) METHODS OF MAKING MEDICAL DEVICES

(75) Inventors: Daniel D. Sims, Arvada, CO (US);
Jeffrey N. Steinmetz, Arvada, CO (US);
Conor P. Mullens, San Antonio, TX (US); Andrew Parker Wood, Marion, TX (US); Christopher E. Banas, Breckenridge, CO (US)

(73) Assignee: Advanced Bio Prosthetic Surfaces, Ltd., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/780,689

(22) Filed: May 14, 2010

(65) Prior Publication Data

US 2011/0056909 A1  Mar. 10, 2011

Related U.S. Application Data

(63) Continuation of application No. 11/343,993, filed on Jan. 31, 2006, now Pat. No. 7,736,687.

(51) Int. Cl.
*B05D 5/00* (2006.01)
*B05D 3/12* (2006.01)

(52) U.S. Cl. ..................... 427/2.24; 427/2.25

(58) Field of Classification Search ............... 427/2.24, 427/2.25, 2.1, 264, 271; 623/1.12, 1.15, 623/1.2, 1.31, 1.27
See application file for complete search history.

(56) References Cited

U.S. PATENT DOCUMENTS

| 4,510,182 | A | 4/1985 | Cornils et al. | 427/162 |
| 4,733,665 | A | 3/1988 | Palmaz | 606/108 |
| 4,739,762 | A | 4/1988 | Palmaz | 623/1.11 |
| 4,751,099 | A | 6/1988 | Niino et al. | 427/34 |
| 4,776,337 | A | 10/1988 | Palmaz | 623/1.11 |
| 4,846,834 | A | 7/1989 | von Recum et al. | 623/11 |
| 5,049,251 | A | 9/1991 | Inone | 204/192 |
| 5,061,914 | A | 10/1991 | Busch et al. | 337/140 |
| 5,084,151 | A | 1/1992 | Vallana | 204/192.11 |
| 5,102,417 | A | 4/1992 | Palmaz | 606/195 |
| 5,133,732 | A | 7/1992 | Wiktor | 606/195 |
| 5,133,845 | A | 7/1992 | Vallana et al. | 204/192 |

(Continued)

FOREIGN PATENT DOCUMENTS

DE  1452370  3/1969

(Continued)

OTHER PUBLICATIONS

Stoeckel, Dieter, et al., "Self-Expanding Nitinol Stents—Material and Design Considerations". European Radiology, 2003, pp. 1-12.*

(Continued)

*Primary Examiner* — Bret Chen
(74) *Attorney, Agent, or Firm* — J. Peter Paredes; Rosenbaum & Silvert, P.C.

(57) ABSTRACT

Scaffold-supported metal or pseudometallic film covers suitable for use as medical devices are disclosed together with methods of fabricating the devices. Methods for making the medical devices consist of either providing or forming a scaffold, then depositing a metallic or pseudometallic film cover onto the scaffold in such a manner as to form an integral, substantially monolithic junction between the deposited cover material and the scaffold.

20 Claims, 12 Drawing Sheets

U.S. PATENT DOCUMENTS

| | | | |
|---|---|---|---|
| 5,158,750 A | 10/1992 | Finicle | 422/102 |
| 5,242,710 A | 9/1993 | Claar et al. | 427/248 |
| 5,277,933 A | 1/1994 | Claar et al. | 427/248.1 |
| 5,329,514 A | 7/1994 | Eguchi et al. | 369/126 |
| 5,370,684 A | 12/1994 | Vallana et al. | 623/1 |
| 5,376,463 A | 12/1994 | Bak et al. | 429/17 |
| 5,387,247 A | 2/1995 | Vallana et al. | 623/2 |
| 5,421,955 A | 6/1995 | Lau et al. | 216/48 |
| 5,456,712 A | 10/1995 | Maginot | 623/1 |
| 5,456,713 A | 10/1995 | Chuter | 623/1 |
| 5,477,864 A | 12/1995 | Davidson | 128/771 |
| 5,514,154 A | 5/1996 | Lau et al. | 606/195 |
| 5,522,882 A | 6/1996 | Gaterud et al. | 623/1 |
| 5,540,820 A | 7/1996 | Terakado et al. | 204/192.3 |
| 5,545,210 A | 8/1996 | Hess et al. | 623/1 |
| 5,556,414 A | 9/1996 | Turi | 606/198 |
| 5,569,295 A | 10/1996 | Lam | 606/198 |
| 5,591,226 A | 1/1997 | Trerotola et al. | 623/1 |
| 5,593,442 A | 1/1997 | Klein | 623/12 |
| 5,603,721 A | 2/1997 | Lau et al. | 606/195 |
| 5,605,714 A | 2/1997 | Dearnaley et al. | 427/2.24 |
| 5,607,445 A | 3/1997 | Summers | 606/198 |
| 5,607,463 A | 3/1997 | Schwartz et al. | 623/1 |
| 5,609,629 A | 3/1997 | Fearnot et al. | 623/1 |
| 5,628,788 A | 5/1997 | Pinchuk | 623/1 |
| 5,630,840 A | 5/1997 | Mayer | 623/1 |
| 5,647,858 A | 7/1997 | Davidson | 604/264 |
| 5,649,951 A | 7/1997 | Davidson | 606/198 |
| 5,656,036 A | 8/1997 | Palmaz | 623/12 |
| 5,665,115 A | 9/1997 | Cragg | 623/1 |
| 5,683,448 A | 11/1997 | Cragg | 623/1 |
| 5,683,453 A | 11/1997 | Palmaz | 623/1 |
| 5,685,961 A | 11/1997 | Pourrezaei et al. | 204/192 |
| 5,690,670 A | 11/1997 | Davidson | 606/198 |
| 5,693,084 A | 12/1997 | Chuter | 623/1 |
| 5,695,517 A | 12/1997 | Marin et al. | 606/198 |
| 5,702,419 A | 12/1997 | Berry et al. | 606/198 |
| 5,723,219 A | 3/1998 | Kolluri | 428/411.1 |
| 5,725,573 A | 3/1998 | Dearnaley et al. | 623/2 |
| 5,728,158 A | 3/1998 | Lau et al. | 623/12 |
| 5,735,892 A | 4/1998 | Myers et al. | 623/1 |
| 5,735,896 A | 4/1998 | Amon et al. | 623/11 |
| 5,744,515 A | 4/1998 | Clapper | 623/113 |
| 5,755,775 A | 5/1998 | Trerotola et al. | 623/1 |
| 5,765,418 A | 6/1998 | Rosenberg | 72/47 |
| 5,772,864 A | 6/1998 | Moller et al. | 205/73 |
| 5,776,161 A | 7/1998 | Globerman | 606/194 |
| 5,780,807 A | 7/1998 | Saunders | 219/121 |
| 5,782,908 A | 7/1998 | Cahalan et al. | 623/1 |
| 5,782,910 A | 7/1998 | Davidson | 623/3 |
| 5,788,558 A | 8/1998 | Klein | 451/136 |
| 5,798,042 A | 8/1998 | Chu et al. | 210/490 |
| 5,811,151 A | 9/1998 | Hendriks et al. | 427/2.24 |
| 5,824,036 A | 10/1998 | Lauterjung | 623/1 |
| 5,824,045 A | 10/1998 | Alt | 623/1 |
| 5,824,049 A | 10/1998 | Ragheb | 623/1 |
| 5,824,054 A | 10/1998 | Khosravi et al. | 623/1 |
| 5,824,056 A | 10/1998 | Rosenberg | 623/1 |
| 5,824,058 A | 10/1998 | Ravenscroft | 623/1 |
| 5,840,009 A | 11/1998 | Fischell et al. | 600/3 |
| 5,843,117 A | 12/1998 | Alt et al. | 606/194 |
| 5,843,164 A | 12/1998 | Frantzen et al. | 623/1 |
| 5,843,289 A | 12/1998 | Lee et al. | 204/192 |
| 5,849,206 A | 12/1998 | Amon et al. | 216/63 |
| 5,855,600 A | 1/1999 | Alt | 23/1 |
| 5,855,802 A | 1/1999 | Acciai et al. | 216/8 |
| 5,855,955 A | 1/1999 | Claar et al. | 427/248 |
| 5,858,556 A | 1/1999 | Eckert et al. | 428/586 |
| 5,866,113 A | 2/1999 | Hendriks et al. | 424/78.17 |
| 5,868,782 A | 2/1999 | Frantzen | 606/198 |
| 5,873,904 A | 2/1999 | Ragheb et al. | 623/1 |
| 5,876,432 A | 3/1999 | Lau et al. | 623/1 |
| 5,879,370 A | 3/1999 | Fischell et al. | 606/198 |
| 5,891,507 A | 4/1999 | Jayaraman | 427/2.25 |
| 5,895,406 A | 4/1999 | Gray et al. | 606/198 |
| 5,897,911 A | 4/1999 | Loefler | 427/225 |
| 5,899,935 A | 5/1999 | Ding | 623/1 |
| 5,902,332 A | 5/1999 | Schatz | 623/1 |
| 5,907,893 A | 6/1999 | Zadno-Azizi | 29/6.1 |
| 5,913,896 A | 6/1999 | Boyle et al. | 623/1 |
| 5,919,225 A | 7/1999 | Lau et al. | 623/1 |
| 5,919,548 A | 7/1999 | Barron et al. | 428/138 |
| 5,925,063 A | 7/1999 | Khosravi | 606/200 |
| 5,925,075 A | 7/1999 | Myers et al. | 623/1 |
| 5,928,279 A | 7/1999 | Shannon et al. | 623/1 |
| 5,932,299 A | 8/1999 | Katoot | 427/508 |
| 5,938,682 A | 8/1999 | Hojeibane et al. | 606/198 |
| 5,938,697 A | 8/1999 | Killion et al. | 623/1 |
| 5,945,153 A | 8/1999 | Dearnaley | 427/2.12 |
| 5,951,881 A | 9/1999 | Rogers et al. | 216/41 |
| 5,955,588 A | 9/1999 | Tsang et al. | 536/21 |
| 5,962,138 A | 10/1999 | Kolluri et al. | 428/411 |
| 5,968,091 A | 10/1999 | Pinchuk et al. | 623/1 |
| 5,972,018 A | 10/1999 | Israel et al. | 606/198 |
| 5,972,027 A | 10/1999 | Johnson | 623/1 |
| 5,972,441 A | 10/1999 | Campbell et al. | 428/34.1 |
| 5,984,905 A | 11/1999 | Dearnaley et al. | 604/265 |
| 6,001,123 A | 12/1999 | Lau | 623/1 |
| 6,004,348 A | 12/1999 | Banas et al. | 623/1 |
| 6,015,429 A | 1/2000 | Lau et al. | 623/1 |
| 6,019,784 A | 2/2000 | Hines | 623/1 |
| 6,022,370 A | 2/2000 | Tower | 606/194 |
| 6,027,526 A | 2/2000 | Limon et al. | 623/1 |
| 6,033,433 A | 3/2000 | Ehr et al. | 623/1 |
| 6,039,755 A | 3/2000 | Edwin et al. | 623/1 |
| 6,042,597 A | 3/2000 | Kveen et al. | 606/198 |
| 6,042,605 A | 3/2000 | Martin et al. | 623/1 |
| 6,056,776 A | 5/2000 | Lau et al. | 623/1 |
| 6,059,808 A | 5/2000 | Boussignac | 606/191 |
| 6,066,167 A | 5/2000 | Lau et al. | 623/1 |
| 6,066,168 A | 5/2000 | Lau et al. | 623/1 |
| 6,066,169 A | 5/2000 | McGuiness | 623/1.16 |
| 6,071,305 A | 6/2000 | Brown et al. | 623/1 |
| 6,074,381 A * | 6/2000 | Dinh et al. | 606/1 |
| 6,086,773 A | 7/2000 | Dufresne et al. | 216/8 |
| 6,096,175 A | 8/2000 | Roth | 204/192 |
| 6,103,320 A | 8/2000 | Matsumoto et al. | 427/478 |
| 6,106,642 A | 8/2000 | DiCarlo et al. | 148/563 |
| 6,124,523 A | 9/2000 | Banas et al. | 623/11 |
| 6,126,793 A | 10/2000 | Sugiyama et al. | 204/192.23 |
| 6,129,756 A | 10/2000 | Kugler et al. | 623/1.27 |
| 6,136,159 A | 10/2000 | Buckfeller et al. | 204/192.3 |
| 6,143,022 A | 11/2000 | Shull et al. | 623/1.13 |
| 6,156,064 A | 12/2000 | Chouinard | 623/1.44 |
| 6,159,239 A | 12/2000 | Greenhalgh | 623/1 |
| 6,165,211 A | 12/2000 | Thompson | 623/1.13 |
| 6,190,404 B1 | 2/2001 | Palmaz et al. | 623/1.15 |
| 6,207,536 B1 | 3/2001 | Matsumoto et al. | 427/478 |
| 6,210,437 B1 | 4/2001 | Frautschi | 623/1.46 |
| 6,214,039 B1 | 4/2001 | Banas et al. | 623/1.13 |
| 6,214,733 B1 | 4/2001 | Sickmiller | 438/691 |
| 6,217,952 B1 | 4/2001 | Sugiyama et al. | 427/577 |
| 6,231,923 B1 | 5/2001 | Teverovsky et al. | 427/535 |
| 6,234,875 B1 | 5/2001 | Pendergrass, Jr. | 451/41 |
| 6,251,132 B1 | 6/2001 | Ravenscroft | 623/1.11 |
| 6,264,684 B1 | 7/2001 | Banas et al. | 623/1.13 |
| 6,312,463 B1 | 11/2001 | Rourke et al. | 623/1.39 |
| 6,322,585 B1 | 11/2001 | Khosravi et al. | 623/1.11 |
| 6,344,053 B1 | 2/2002 | Boneau | 623/1.11 |
| 6,344,054 B1 | 2/2002 | Parodi | 623/1.13 |
| 6,346,119 B1 | 2/2002 | Kuwahara et al. | 623/1.13 |
| 6,348,066 B1 | 2/2002 | Pinchuk et al. | 623/1.16 |
| 6,352,553 B1 | 3/2002 | Van der Burg | 623/1.23 |
| 6,355,058 B1 | 3/2002 | Pacetti et al. | 623/1.15 |
| 6,361,637 B2 | 3/2002 | Martin et al. | 156/187 |
| 6,379,383 B1 | 4/2002 | Palmaz et al. | 623/1.49 |
| 6,383,214 B1 | 5/2002 | Banas et al. | 623/1.14 |
| 6,391,052 B2 | 5/2002 | Buirge et al. | 623/1.47 |
| 6,398,802 B1 | 6/2002 | Yee | 623/1.13 |
| 6,416,535 B1 | 7/2002 | Lazarus | 623/1.11 |
| 6,428,569 B1 | 8/2002 | Brown | 623/1.15 |
| 6,436,132 B1 | 8/2002 | Patel et al. | 623/1.13 |
| 6,443,981 B1 | 9/2002 | Colone et al. | 623/1.13 |
| 6,451,047 B2 | 9/2002 | McCrea et al. | 623/1.13 |
| 6,475,232 B1 | 11/2002 | Babbs et al. | 623/1.13 |
| 6,488,701 B1 | 12/2002 | Nolting et al. | 623/1.13 |
| 6,500,203 B1 | 12/2002 | Thompson et al. | 623/1.13 |

| | | | | |
|---|---|---|---|---|
| 6,527,919 | B1 | 3/2003 | Roth | 204/192.15 |
| 6,533,905 | B2 | 3/2003 | Johnson et al. | 204/192.15 |
| 6,537,310 | B1 | 3/2003 | Palmaz et al. | 623/1.13 |
| 6,695,865 | B2 | 2/2004 | Boyle et al. | 606/200 |
| 6,709,455 | B1 | 3/2004 | Chouinard | 623/1.32 |
| 6,733,870 | B2 | 5/2004 | Enlow et al. | 428/207 |
| 6,746,890 | B2 | 6/2004 | Gupta et al. | 438/50 |
| 6,926,733 | B2* | 8/2005 | Stinson | 623/1.15 |
| 6,936,066 | B2 | 8/2005 | Palmaz et al. | 606/108 |
| 7,407,672 | B2* | 8/2008 | Peddareddigari et al. | 424/520 |
| 7,458,991 | B2* | 12/2008 | Wang et al. | 623/23.55 |
| 7,736,687 | B2* | 6/2010 | Sims et al. | 427/2.1 |
| 2002/0017503 | A1 | 2/2002 | Banas et al. | 219/69.11 |
| 2003/0004567 | A1 | 1/2003 | Boyle et al. | 623/1.16 |
| 2003/0059640 | A1 | 3/2003 | Marton et al. | 428/544 |
| 2003/0070469 | A1* | 4/2003 | Kokish | 72/402 |
| 2003/0074053 | A1 | 4/2003 | Palmaz et al. | 623/1.15 |
| 2003/0083646 | A1 | 5/2003 | Sirhan et al. | 604/891.1 |
| 2003/0153981 | A1* | 8/2003 | Wang et al. | 623/22.21 |
| 2003/0218735 | A1* | 11/2003 | Trozera | 355/104 |
| 2004/0016120 | A1 | 1/2004 | Boland | 29/886 |
| 2004/0086496 | A1* | 5/2004 | Peddareddigari et al. | 424/93.21 |
| 2004/0098094 | A1 | 5/2004 | Boyle et al. | 623/1.13 |
| 2004/0186554 | A1 | 9/2004 | Banas et al. | 623/1.15 |
| 2005/0255230 | A1 | 11/2005 | Clerc et al. | 427/2.1 |
| 2006/0013850 | A1 | 1/2006 | Domb | 424/422 |
| 2006/0165872 | A1* | 7/2006 | Chappa et al. | 427/2.24 |
| 2006/0188543 | A1* | 8/2006 | Feng | 424/423 |
| 2007/0034528 | A1* | 2/2007 | Diaz et al. | 205/686 |
| 2010/0274347 | A1* | 10/2010 | Boyle | 623/1.15 |
| 2011/0000070 | A1* | 1/2011 | Wu | 29/428 |

FOREIGN PATENT DOCUMENTS

| | | |
|---|---|---|
| EP | 0 400 947 | 12/1990 |
| EP | 0 442 303 | 8/1999 |
| JP | 51055724 | 5/1976 |
| JP | 07090436 | 4/1995 |
| JP | 11267462 | 10/1999 |
| WO | WO97/07257 | 2/1997 |
| WO | WO97/44692 | 11/1997 |
| WO | WO98/13537 | 4/1998 |
| WO | WO98/45506 | 10/1998 |
| WO | WO99/23977 | 5/1999 |
| WO | WO99/62432 | 12/1999 |
| WO | WO00/04204 | 1/2000 |
| WO | WO00/20146 | 4/2000 |
| WO | WO01/53559 | 7/2001 |
| WO | WO01/55473 | 8/2001 |
| WO | WO01/56502 | 8/2001 |
| WO | WO03/013337 | 2/2003 |
| WO | WO2004/22122 | 3/2004 |

OTHER PUBLICATIONS

Ma, Peter X., et al., "Biodegradable Polymer Scaffolds with Well-Defined Interconnected Spherical Pore Network". Tissue Engineering, vol. 7, No. 1, 2001, pp. 23-33.*

AMETEK Specialty Metal Products, "Sputtering Targets High-Quality, Thin Film Materials" online at www.ametek84.com/fd-sputtering.html, pp. 1-3.

Banning, Larry G., M.D., et al., "The Experimental Use of Steel Mesh Tubes for the Replacement of Arterial Segments" Presented at the Third Scientific Meeting of the North American Chapter of the International Society of Angiology, Atlantic City, NJ, pp. 69-75 (1995).

Busch, J.D., et al., "Shape Memory Properties in NiTI Sputter-deposited Film" J Appl. Phys 68(12): 6224-6226 (1990).

Buchaillot, L., et al., "Constitutive Parts of a Shape Memory Alloy Titanium Nickel Thin Film Catheter" Proceedings of the Second International Conference on Shape Memory and Superelastic Technologies Asilomar Conference Center, Pacific Grove, California, USA, pp. 183-188 (1997).

Cejna, M., et al., "Primary implantation of polyester-covered stent-grafts for transjugular introhepatic portosystemic stent shunts (TIPSS): A pilot study", Cardiovasc Intervent Radiol, 22:305-310 (1999).

Chu, J.P., et al., "Deposition and characterization of TiNi-base thin films by sputtering" Materials Science and Engineering, A277:11-17 (2000).

Curtis, et al., "Reactions of Biological Cells to Nanostructures" AVS 46th International Symposium, Paper BI-WeM2(1999).

Davies, P.F., et al., "Quantitative studies of endothelial cell adhesion. Directional remodeling of focal adhesion sites in response to flow forces" J. Clin invest., 93(5): 2031-2038 (1994).

Davies, P.F., et al., "Endothelial cell adhesion in real time. Measurements in vitro by tandem scanning confocal image analysis" J. Clin Invest, 91(6): 2640-2652 (1991).

Daw, R., et al., "Endothelial Cell Organization on Micropatterned Protein Surfaces", AVS 47th International Symposium, Paper No. BI-WeP21 (2000).

Ensinger, W., "The influence of ion irradiation during film growth on the chemical stability of film/substrate systems" Surface and Coatings Technology, 80: 35-48 (1996).

Fancey, K.S., et al., "Relative importance of bombardment energy and intensity in ion plating" (Abstract) Journal of Vacuum Science & Technology A: Vacuum, Surface and Films, 13(2): 428-435 (1995).

Gisser, K., et al., "Oriented nickel-tetanium shape memory alloy films prepared by annealing during deposition" (Abstract) Applied Physics Letters, 61(14): 1632-1634.

Goldberg, F., et al., "The effects of ion irradiation on NiTi shape memory alloy thin films" Proceedings of the Second International Conference on Shape Memory and Superelastic Technologies Asilomar Conference Center, Pacific Grove, California, USA, pp. 177-182 (1997).

Gordon, et al., "Liquid sources for chemical vapor deposition of group 6 metals and metal nitrides" www.techtransfer.harvard.edu/cgi-bin/TALSearch.cgi?full_report=1&case=3, Case No. 1709.

Haskal, Ziv J., M.D., "Improved patency of transjugular intrahepatic portosystemic shunts in humans: creation and revision with PTFE stent-grafts[1]" Radiology, 213(3): 759-766 (1999).

Haskal, Z.J., et al., "Porous and nonporous polycarbonate urethane stent-grafts for TIPS formation: biologic responses" (Abstract), J. Vasc. Interv. Radiol, 10(9): 1255-1263 (1999).

Houston, J. E., "The nanomechanical properties of thin films" AVS 47th International Symposium, Paper No. TF-TuA1 (2000).

Inoue, K., M.D., et al, "Aortic arch reconstruction by transluminally placed endovascular branched stent graft" Circulation, pp. II316-II321 (1999).

Ishida, A., et al., "Microstructure of Ti-rich TiNi thin films" Proceedings of the Second International Conference on Shape Memory and Superelastic Technologies Asilomar Conference Center, Pacific Grove, California, USA, pp. 161-166 (1997).

Johnson, A.D., et al., "Recent progress in the application of thin film shape memory alloys" Proceedings of the First International Conference on Shape Memory and Superelastic Technologies Asilomar Conference Center, Pacific Grove, California, USA, pp. 299-310 (1994).

Johnson, A.D., et al., "Applications of shape-memory alloy thin films" Proceedings of the Second International Conference on Shape Memory and Superelastic Technologies Asilomar Conference Center, Pacific Grove, California, USA, pp. 1-8 (1997).

Johnson, et al., "progress in thin film shape memory-microactuators", www.sma-mems.com/recent.htm (Overview), pp. 1-5.

Kalman, Peter G., M.D., "Stent-graft repair for abdominal aortic aneurysm" CMAJ, 161(9): 1133.

Kusano, E., et al., "Anomalous plastic and elastic behaviors of sputter-deposited TiN with 10 or 20 inserted thin Al layers evaluated by nanoindentation", AVS 47th International Symposium. Paper No. TF-TuA3 (2000).

Mattox, D., "Concise history of vacuum coating technology, Part 2: 1940 to 1975" www.svc.org/Historyof_Vac2.html, pp. 1-15.

Mrksich, M., "Model surfaces for studying and controlling the adhesion of cells" AVS 47th International Symposium, Invited Paper No. BI+EL-TuA1 (2000).

Nishikawa, T., et al., "Tissue formation of hepatocytes on microporous films of polylactide", AVS 47th International Symposium, Paper No. BI+EL-TuA10 (2000).

Pingshan, Q., et al., "The effect of HCD technological factors on the NiTi SMA film thickness" Proceedings of the Second International

*Conference on Shape Memory and Superelastic Technologies Asilomar Conference Center, Pacific Grove, California, USA*, pp. 173-176 (1997).

Quandt, E., et al., "Sputter-deposition of Tine, TiNi, TiNiPd and TiPd films displaying the two-way shaped-memory effect" *Sensors and Actuators*, A 53, pp. 434-439 (1996).

Serruys, P.W., et al., "Handbook of Coronary Stents" *M.J.B. Third Ed.* (2000).

Stolf, N.A., et al., "Self-expanding endovascular stent-graft implant for treatment of descending aortic diseases" (Abstract), *J. Card, Surg.* 14(1): 9-15 (1999).

Sutherland, D.S., et al., "Cell response to chemically and topographically modified surfaces" *AVS 47th international Symposium, Paper No, BI+EL-TuA3* (2000).

Uhrmeister, P., et al., "Stents for the treatment of aortic aneurysms. Review of devices, technique and results" (Abstract) *Thromb Haemost*, 820(1 Suppl): 171-175 (1999).

Vroman, L., "The Importance of surfaces in contact phase reactions" *Seminars of Thrombosis and Hemostasis* 13(1): 79-85 (1987).

Walker, J.A., et al., "Thin-film processing of TiNi shape memory alloy" *Sensors and Actuators*, A21-A23: 243-246 (1990).

Weixin, H., et al., "The characteristics of NiTi HCD-deposited SMA films", *Proceedings of the Second International Conference on Shape Memory and Superelastic Technologies Asilomar Conference Center, Pacific Grove, California, USA*, pp. 167-172 (1997).

Ye, et al., "Bioresorbable microporous stents deliver recombinant adenovirus gene transfer ventors to the arterial wall" *Annals of Biomedical Engineering*, 26: 298-408 (1998).

Zheng, H., et al., "Clinical) Experience With a New Biocompatible Phosphorylcholine-Coated Coronary Stent" (Abstract) *J. Invasive Cardiol*, 11(10): 608-614 (1999).

AVS 46th International Symposium, Paper BI-WeM5, "Biocompatibility of cardiac cells on silane-modified surfaces" (1999).

AVS 46th International Symposium, Paper No. BI-FrM10, "Biofilm—titanium chemistry of adhesion using x-ray photoelectron spectroscopy" (1999).

AVS 46th International Symposium, Paper No. BI-WeM7, "Biofunctionalization of surfaces with peptide amphilphiles" (1999).

AVS 46th International Symposium, Paper No. BI-FrM10, "Nanoscale patterning of gold for attachment of supported lipid bilayers" (1999).

AVS 46th International Symposium, Paper No. BI-WeM9, "Plasma copolymer surfaces for cell structure" (1999).

AVS 46th International Symposium, Paper No. BI-FrM2, "Plasma co-polymer surfaces for the controlled adsorption of common proteins" (1999).

http://www.glue.umd.edu/~astan/avs01.htm, "Amorphous carbon and C:N. thin films".

http://www.glue.umd.edu/~astan/avs04.htm, "Focused ion beam non-fabrication".

http://www.phytis.com/stent4.htm, "Adhesion of bovine serus albumin on coated DLC (diamond-like) and uncoated (SiO2 / TiO2.) sensor chips", pp. 1-2.

http://www.phytis.com/stents0.htm, "Benefits from diamond-Like coated stainless steel stents", pp. 1-2.

http://www.phytis.com/direcuse.htm, "Directions for use, Diamond AS7 stent", pp. 1-8.

http://www..phytis.com/stent9.htm, "Expertise concerning the implementation of the Phytis Diamond as Stent performed at the institute for experimental medicine (IEM)", pp.1.

http://www.phytis.com/stent6.htm, "Flow cytometric investigation", pp. 1-3.

http://www.phytis.com/stent3.htm, "Invulnerability and resistance of DLC-coating",pp. 1-3.

http://www.phytis.com/stent5.htm, "Material in use and its biocompatibility", pp. 1-2.

http://www.phytis.com/content.htm, "Phytis L.D.A. home page information", pp. 1-15.

http://www.phytis.com/stent2.htm, "Pre-clinical and clinical evaluation", pp. 1B2.

http://www.phytis.com/risk.htm, "Risk analysis of stents with a diamond-like coated surface for use in prosthetic implants",, pp. 1-6.

http://www.phytis.com/liter.htm, "Stents: Literature", pp. 1-8.

http://www.phytis.com/stentl.htm, "The new Phytis stent", pp. 1-2.

IBM Technical Disclosure Bulletin, "Multicomponent film deposition by target biasing", pp. 1-2 (1980).

Ion Beam-Assisted, Electron Beam Physical Vapor (EB-PVD) Deposition, Penn State Applied Research Laboratory, "Multilayer ceramic/metallic coatings" pp. 1-4 (1997).

Journal of Vacuum Science and Technology, JVST A Online, "Vacuum conditions for sputtering thin Film TiNi" (Abstract) pp. 1-2.

TiNi Alloy Company (online), "Thin film shape memory alloy microactuators".

www.nasatech.com/Briefs/Mar02/LEW17079.html. "Photolithographic fine patterning of difficult-to-etch metals".

www.techtransfer.harvard.edu/cgi-bin/TALSearch.cgi?full_report=1&case=72, "Fabrication of small-scale coils and bands as photomasks on optical fibers for generation of in-fiber gratings, electromagnets as micro-NMR coils, microtransformers and intra-vascular stents", Case No. 1263.

US 6,413,270, 07/2002, Thornton et al. (withdrawn)

* cited by examiner

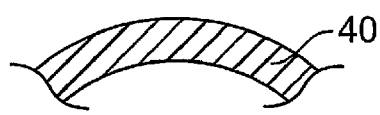
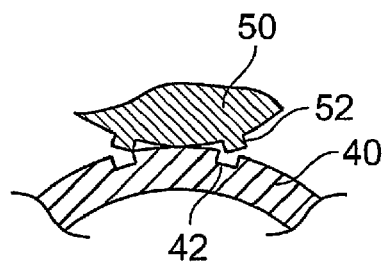
FIG. 2A                 FIG. 2B
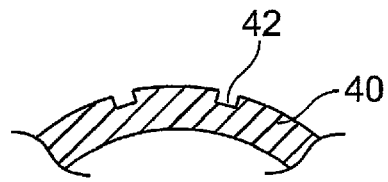
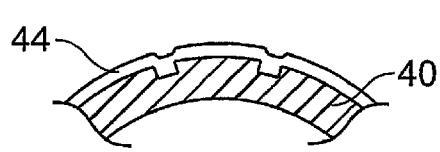
FIG. 2C                 FIG. 2D
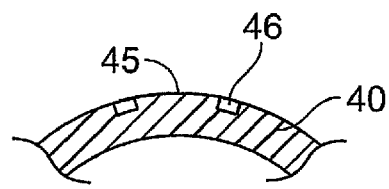
FIG. 2E                 FIG. 2F
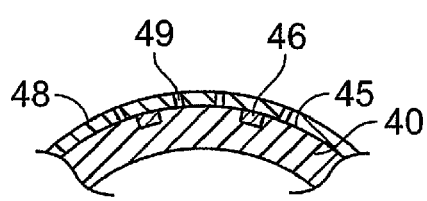
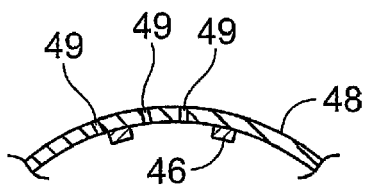
FIG. 2G                 FIG. 2H

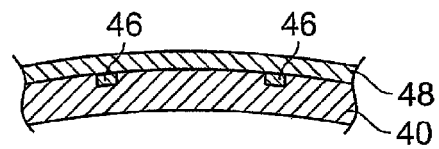
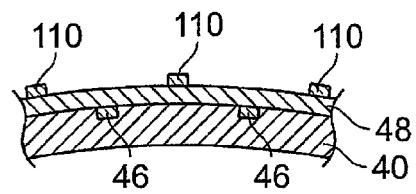
FIG. 8A  FIG. 8B
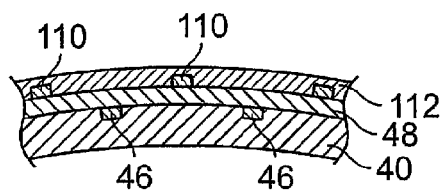
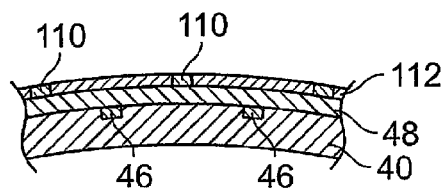
FIG. 8C  FIG. 8D
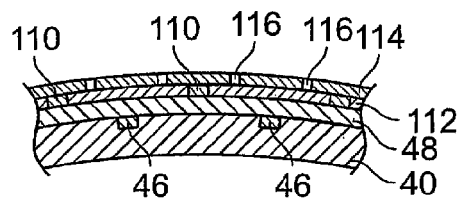
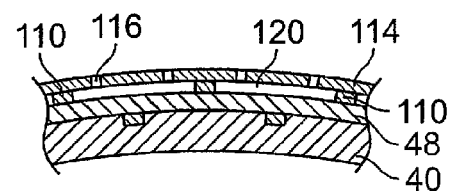
FIG. 8E  FIG. 8F
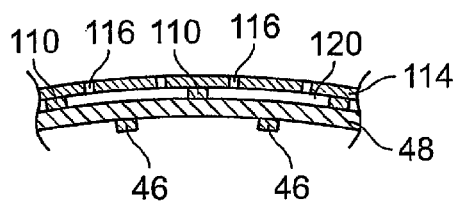
FIG. 8G

METHODS OF MAKING MEDICAL DEVICES

CROSS-REFERENCE TO RELATED APPLICATIONS

This application is a continuation of U.S. patent application Ser. No. 11/343,993, filed Jan. 31, 2006, which issued as U.S. Pat. No. 7,736,687 on Jun. 15, 2010, which is related to U.S. patent application Ser. No. 10/289,974, filed Nov. 6, 2002, which issued as U.S. Pat. No. 7,491,226 on Feb. 17, 2009, which is a divisional application of U.S. patent application Ser. No. 09/532,164, filed Mar. 20, 2000, which issued as U.S. Pat. No. 6,537,310 on Mar. 25, 2003, which is continuation-in-part of U.S. patent application Ser. No. 09/443,929, filed Nov. 19, 1999, which issued as U.S. Pat. No. 6,379,383 on Apr. 30, 2002, all incorporated by reference herein.

BACKGROUND OF THE INVENTION

The present invention relates generally to methods of fabricating medical devices by vacuum deposition of device-forming materials onto a suitable substrate. More particularly, the present invention relates to methods of fabricating structural scaffolds, coverings for scaffolds and covered scaffolds.

The present invention also pertains generally to implantable medical devices and, more particularly, to implantable medical devices which are capable of being implanted utilizing minimally-invasive delivery techniques.

Conventional endoluminal stents and stent-grafts are frequently used after a percutaneous transluminal angioplasty (PTA) or percutaneous transluminal coronary angioplasty (PTCA) procedure which dilitates an occluded, obstructed or diseased anatomical passageway to provide structural support and maintain the patency of the anatomical passageway. An example of this is the post-angioplasty use of intravascular stents to provide a structural support for a blood vessel and reduce the incidence of restenosis. A principal, but non-limiting, example of the present invention are covered intravascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma. Covered stents are delivered and deployed under similar circumstances and are utilized to maintain patency of an anatomic passageway, for example, by reducing restenosis following angioplasty, or when used to exclude an aneurysm, such as in aortic aneurysm exclusion applications. Embolic protection devices, which generally consist of a porous flexible material coupled to an expansive structural scaffold, are an example of alternative devices capable of being fabricated by the present invention. For purposes of illustration only, and without any intent to so limit the present invention, hereinafter reference will be made to endoluminal stents and covered stents. However, those of ordinary skill in the art will understand that alternative types of medical devices which are susceptible of being fabricated by the methods of the present invention.

While endoluminal stenting has successfully decreased the rate of restenosis in angioplasty patients, it has been found that a significant restenosis rate continues to exist in spite of the use of endoluminal stents. It is generally believed that the post-stenting restenosis rate is due, in major part, to the non-regrowth of the endothelial layer over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis.

Most endoluminal stents are manufactured of metals that fail to promote redevelopment of a healthy endothelium and/or are known to be thrombogenic. In order to increase the healing and promote endothelialization, while maintaining sufficient dimensional profiles for catheter delivery, most stents minimize the metal surface area that contacts blood. Thus, in order to reduce the thrombogenic response to stent implantation, as well as reduce the formation of neointimal hyperplasia, it would be advantageous to increase the rate at which endothelial cells form endothelium proximal and distal to the stent situs, migrate onto and provide endothelial coverage of the luminal surface of the stent which is in contact with blood flow through the vasculature.

Current covered stents are essentially endoluminal stents with a discrete covering on either or both of the luminal and abluminal surfaces of the stent that occludes the open spaces, or interstices, between adjacent structural scaffold members of the endoluminal stent. It is known in the art to fabricate stent-grafts by covering the stent with endogenous vein or a synthetic material, such as woven polyester known as DACRON, or with expanded polytetrafluoroethylene. Additionally, it is known in the art to cover the stent with a biological material, such as a xenograft or collagen. A primary purpose for covering stents with grafts is to reduce the thrombogenic effect of the stent material and prevent embolic material from passing through stent interstices and into the general circulation. However, the use of conventional graft materials has not proven to be a complete solution to enhancing the healing response of conventional stents.

U.S. Pat. No. 6,312,463 describes a variation of a prosthesis in that the prosthesis includes a tubular element that is a thin-walled sheet having temperature-activated shape memory properties. The tubular element is supported by a support element that includes a plurality of struts. The tubular element is described as a thin-walled sheet preferably having of a coiled-sheet configuration with overlapping inner and outer sections.

Current metallic vascular devices, such as stents, are made from bulk metals made by conventional methods, and stent precursors, such as hypotubes, are made by many steps that introduce processing aides to the metals. For example, olefins trapped by cold drawing and transformed into carbides or elemental carbon deposit by heat treatment, typically yield large carbon rich areas in 316L stainless steel tubing manufactured by cold drawing process. The conventional stents have marked surface and subsurface heterogeneity resulting from manufacturing processes (friction material transfer from tooling, inclusion of lubricants, chemical segregation from heat treatments). This results in formation of surface and subsurface inclusions with chemical composition and, therefore, reactivity different from the bulk material. Oxidation, organic contamination, water and electrolytic interaction, protein adsorption and cellular interaction may, therefore, be altered on the surface of such inclusion spots. Unpredictable distribution of inclusions such as those mentioned above provide an unpredictable and uncontrolled heterogeneous surface available for interaction with plasma proteins and cells. Specifically, these inclusions interrupt the regular distribution pattern of surface free energy and electrostatic charges on the metal surface that determine the nature and extent of plasma protein interaction. Plasma proteins deposit nonspecifically on surfaces according to their relative affinity for polar or non-polar areas and their concentration in blood. A replacement process known as the Vroman effect, Vroman L., The importance of surfaces in contact phase reactions, Seminars of Thrombosis and Hemostasis 1987; 13(1): 79-85, determines a time-dependent sequential replacement of predominant proteins at an artificial surface, starting with albumin, following with IgG, fibrinogen and ending with high molecular weight kininogen. Despite this variability in surface adsorption specificity, some of the adsorbed proteins have receptors available for cell attachment and therefore constitute adhesive sites. Examples are: fibrinogen glycoprotein receptor IIbIIIa for platelets and fibronectin RGD sequence for many blood activated cells. Since the coverage of an artificial surface with endothelial cells is a favorable endpoint in the healing process, favoring endothelialization in device design is desirable in implantable vascular device manufacturing.

Normally, endothelial cells (EC) migrate and proliferate to cover denuded areas until confluence is achieved. Migration, quantitatively more important than proliferation, proceeds under normal blood flow roughly at a rate of 25 μm/hr or 2.5 times the diameter of an EC, which is nominally 10 μm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules (such as RGD, mentioned above). An EC has roughly 16-22% of its cell surface represented by integrin clusters. Davies, P. F., Robotewskyi A., Griem M. L. Endothelial cell adhesion in real time. J. Clin. Invest. 1993; 91:2640-2652, Davies, P. F., Robotewski, A., Griem, M. L., Qualitative studies of endothelial cell adhesion, J. Clin. Invest. 1994; 93:2031-2038. This is a dynamic process, which implies more than 50% remodeling in 30 minutes. The focal adhesion contacts vary in size and distribution, but 80% of them measure less than 6 $\mu m^2$, with the majority of them being about 1 $\mu m^2$, and tend to elongate in the direction of flow and concentrate at leading edges of the cell. Although the process of recognition and signaling to determine specific attachment receptor response to attachment sites is incompletely understood, regular availability of attachment sites, more likely than not, would favorably influence attachment and migration. Irregular or unpredictable distribution of attachment sites, that might occur as a result of various inclusions, with spacing equal or smaller to one whole cell length, is likely to determine alternating hostile and favorable attachment conditions along the path of a migrating cell. These conditions may vary from optimal attachment force and migration speed to insufficient holding strength to sustain attachment, resulting in cell slough under arterial flow conditions. Due to present manufacturing processes, current implantable vascular devices exhibit such variability in surface composition as determined by surface sensitive techniques such as atomic force microscopy, X-ray photoelectron spectroscopy and time-of-flight secondary ion mass spectroscopy.

There have been numerous attempts to increase endothelialization of implanted stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene, U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299).

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc., customarily used in manufacturing stents, initiates platelet deposition and activation of the coagulation cascade, which results in thrombus formation. The thrombus formation can range from partial covering of the luminal surface of the stent to a completely occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis.

Although the problems of thrombogenicity and re-endothelialization associated with stents have been contemplated by the art in various manners which cover the stent, with either a biologically active or an inactive covering which is less thrombogenic than the stent material and/or which has an increased capacity for promoting re-endothelialization of the stent situs, the problems remain. These solutions require the use of existing stents as substrates for surface derivatization or modification, and each of the solutions result in a biased or laminate structure built upon the stent substrate. These prior art coated stents are susceptible to delaminating and/or cracking of the coating when mechanical stresses of transluminal catheter delivery and/or radial expansion in vivo. Moreover, because these prior art stents employ coatings applied to stents fabricated in accordance with conventional stent formation techniques, e.g., cold-forming metals, the underlying stent substrate is characterized by uncontrolled heterogeneities on the surface thereof. Thus, coatings merely are laid upon the heterogeneous stent surface, and inherently conform to the topographical heterogeneities in the stent surface and mirror these heterogeneities at the blood contact surface of the resulting coating. This is conceptually similar to adding a coat of fresh paint over an old coating of blistered paint; the fresh coating will conform to the blistering and eventually, blister and delaminate from the underlying substrate. Thus, topographical heterogeneities are typically telegraphed through a surface coating. Chemical heterogeneities, on the other hand, may not be telegraphed through a surface coating but may be exposed due to cracking or peeling of the adherent layer, depending upon the particular chemical heterogeneity.

Heretofore, medical devices consisting of covered scaffolds have been fabricated by separately forming the scaffold and the cover, then joining the cover material to the supporting scaffold such as by sutures, forming thermal joints, such as welds, adhesives or the like. Fabrication of covered scaffolds by depositing successive layers of materials onto a substrate has, heretofore been unknown in the art. Furthermore, the art still has a need for a covered stent device in which a structural support, such as a stent, defines openings which are subtended by a thin film layer, with both the stent and the subtending thin film being formed, at least in portions thereof, as a single, integral, monolithic structure and fabricated of metals or of metal-like materials.

SUMMARY OF THE INVENTION

Alternative embodiments disclosed herein relate to medical devices including both a structural scaffold member for support and a thin film cover, preferably an integral cover, including endoluminal grafts, covered stent devices including stent-grafts and stent-graft-type devices, and embolic filters, each of which are fabricated entirely of biocompatible metals or of biocompatible materials which exhibit biological response and material characteristics substantially the same as biocompatible metals, referred to herein synomously as "pseudometallic materials" or "pseudometals", such as for example composite materials. Both the structural scaffold member and thin film cover are fabricated of biocompatible metals or of pseudometallic materials. Such devices are delivered through anatomical passageways using minimally invasive delivery techniques. In accordance with one embodiment, the medical devices are fabricated by physical vapor deposition processes in which the covering and the scaffold are integrally and monolithically joined to one another during the deposition process. In accordance with an alternative embodiment, the medical devices are fabricated by electrochemical deposition of metals onto a suitable substrate.

One embodiment is to provide methods for fabricating medical devices by depositing device-forming materials onto a suitable substrate to form a structural scaffold and a covering membrane or film over the structural scaffold. In accordance with this embodiment, both the structural scaffold and the covering membrane are formed in operable association with one another on the deposition substrate.

A further embodiment provides an implantable device which consists of a microporous thin film covering comprised of a metallic or pseudometallic material and an underlying structural support made of a metallic or pseudometallic material, both formed in conjunction with one another on a deposition substrate. The microporous metallic or pseudometallic thin film covering is also described in co-pending, commonly assigned U.S. Pat. No. 6,936,066, issued Aug. 30, 2005, which is hereby expressly incorporated by reference as describing the microporous thin film covering. While both the microporous thin film covering and the underlying structural support may be fabricated from many different materials, in accordance with one embodiment, both the microporous thin film covering and the underlying structural scaffold support are fabricated from metallic or pseudometallic materials having shape memory and/or superelastic properties. More preferably, the metal used to fabricate both the microporous thin film covering and the underlying structural support of inventive implantable endoluminal graft is Nitinol. The underlying structural support, without the microporous thin film covering, may be a stent, an embolic filter scaffold or other type of medical scaffold. The underlying structural support can assume any commonly known geometries in the art that possess requisite hoop strength, circumferential compliance or longitudinal flexibility for both endoluminal delivery and/or acting as an in vivo prosthesis. In a preferred embodiment, the structural support element adopts a geometry that includes at least a pair of cylindrical elements and interconnecting members that join adjacent cylindrical elements at nearly identical angular points along the circumference of the cylindrical elements.

In another embodiment, an implantable graft includes a microporous thin film covering comprised of a metallic material which has shape memory and/or pseudoelastic properties and a structural support element underlying the microporous thin film covering. "Pseudoelastic properties" is used herein to refer to the ability of the metallic material to undergo "pseudoelastic deformation". In a preferred aspect, the structural support element has shape memory properties that allow the structural support element to undergo a phase transition from martensite to austenite phase at body temperature. During this phase transition, the structural support element self-expands from an initial, delivery diameter to an enlarged expanded diameter for its intended in vivo use. The shape memory expansion of the structural support element exerts a radially expansive force upon the microporous thin film covering, thereby causing the microporous thin film to radially expand with the structural support element. While the expansion of the microporous thin film appears to be plastic, because the microporous thin film is a shape memory material, the expansion is actually fully recoverable above the transition temperature of the material, and is, therefore, "pseudoplastic".

In still another embodiment, an implantable endoluminal graft is comprised of a microporous thin film covering comprised of a shape memory alloy having an austenite phase transition temperature, $A_s$, greater than 37° C. and a structural support element underlying the microporous thin film covering that is comprised of a shape memory alloy that has an austenite phase transition temperature less than 37° C. Thus, in both the delivery diameter and the implanted expanded diameter, the microporous thin film remains in a martensite state, while the structural element undergoes a phase transition from martensite to austenite at body temperature.

Another embodiment is an implantable endoluminal graft wherein the structural support element is monolithically connected to the microporous thin film covering at least one point of contact between the microporous thin film covering and the structural support element. Preferably, the at least one point of contact is located at either near a proximal end or distal end of the microporous thin film covering and corresponding end of the structural support element. Even more preferably, the at least one point of contact is located at near a distal end of the microporous thin film covering and structural support element.

In another embodiment, the implantable endoluminal graft includes a microporous thin film covering comprised of a uniform pattern of openings throughout the surface of the microporous thin film covering. The openings can be selected from common geometric shapes including a circle, triangle, ellipsoid, diamond, star, clover, rectangle, square, or straight or curved lines.

The structural scaffold member may consist of any type of structural scaffold member. In accordance with the several embodiments, the structural support member may be selected from the group of stents, embolic protection filter supports, valvular prostheses, septal occluders, vascular occluders, shunts or the like. In accordance with an embodiment, the structural scaffold support is preferably generally tubular in configuration, and has an inner or luminal wall surface and an outer or abluminal wall surface and a central lumen passing along the longitudinal axis of the structural support member and is comprises of a plurality of interconnected expansive structural scaffold members. The structural support member may be comprised of a wide variety of geometric configurations and constructions, as are known in the art. For example, the structural support member may assume a balloon expandable slotted configuration of U.S. Pat. Nos. 4,733,665, 4,739, 762, 4,776,337 or 5,102,417 or the structural support member may be configured as a plurality of self-expanding interwoven wire members or it may assume any of the wall geometries disclosed in Serruys, P. W., Kutryk, M. J. B., *Handbook of Coronary Stents*, $3^{rd}$ Ed. (2000). Each of the structural support member designs, structural support member materials, structural support member material characteristics, e.g., balloon expandable, self-expanding by spring tension of the material, self-expanding by shape memory properties of the structural support member material, or self-expanding by superelastic properties of the structural support member material are well known to one of ordinary skill in the art and may be used with the implantable graft of one embodiment.

An aspect of one embodiment is a method for creating materials specifically designed for manufacture of grafts, stents, covered stents, stent-grafts, embolic filters or other medical devices capable of delivery by minimally invasive techniques. According to one embodiment, the manufacture of the materials used to form the medical devices is controlled to attain a regular, homogeneous atomic and molecular pattern of distribution along their surfaces. This avoids the marked variations in surface composition, creating predictable oxidation and organic adsorption patterns and has predictable interactions with water, electrolytes, proteins and cells. Particularly, EC migration is supported by a homogeneous distribution of binding domains that serve as natural or implanted cell attachment sites, in order to promote unimpeded migration and attachment. Based on observed EC attachment mechanisms such binding domains should have a repeating pattern along the blood contact surface of no less than about a 1 μm radius and about a 2 μm border-to-border spacing between binding domains. Ideally, the inter-binding domain spacing is less than the nominal diameter of an endothelial cell in order to ensure that at any given time, a portion of an endothelial cell is in proximity to a binding domain.

In accordance with one particular embodiment, there is provided a covered stent device in which there is at least one of a plurality of structural scaffold members that provides a primary means of structural support for the covered stent device. The plurality of structural scaffold members is spaced apart to form open regions or interstices between adjacent structural scaffold members. In one embodiment, a web of material, that is the same or similar to the material which forms the plurality of structural scaffold members, subtends the interstices or open regions between adjacent structural scaffold members. The web may be formed within all or a portion of the interstitial area or open regions between the plurality of structural support members. Both the plurality of interconnected structural scaffold members and the web may be formed of initially substantially planar materials or of initially substantially cylindrical materials.

Still another embodiment provides a method of fabricating the medical device which entails depositing a first layer of device-forming material onto a substrate having a at least one of a plurality of patterned recesses defining the geometry of the structural scaffold, then planarizing the deposited first layer to the surface of the substrate, such that only the device-forming material in the recesses remains, then depositing a second layer of device-forming material onto the substrate and the first layer, then patterning a plurality of openings in the second layer, then removing the substrate from the deposited and patterned second layer and first layer of device-forming material to provide the formed medical device.

A further aspect of one embodiment provides a method of fabricating a medical device which includes the step of disposing a structural scaffold, such as a stent or an expansible framework for an embolic filter, onto a substrate, vacuum depositing a sacrificial material onto the structural scaffold and the substrate, planarizing the sacrificial material to an outer surface of the structural scaffold, depositing a cover material onto the planarized sacrificial material and the structural scaffold, patterning openings in deposited cover material, and removing the sacrificial material and the substrate to release the formed medical device.

Devices, such as covered stents, drug-eluting stents, embolic filters, supported grafts, shunts, or the like may be made by any of the methods disclosed herein. Common to such devices, there is provided a cover member or graft formed as a discrete thin sheet or tube of biocompatible metal or metal-like materials. A plurality of openings are formed which pass transversely through the cover member. The plurality of openings may be random or may be patterned. The size of each of the plurality of openings may be such as to permit cellular migration through each opening, without permitting fluid flow there through, but various cells or proteins may freely pass through the plurality of openings to promote device healing in vivo. Alternatively, for example as in the case of embolic filter, blood must pass through and therefore the size of each of the openings will be larger to accommodate blood flow therethrough.

In accordance with another embodiment, there is provided an implantable endoluminal device that is fabricated from materials that present a blood or tissue contact surface that is substantially homogeneous in material constitution. More particularly, the present invention provides an endoluminal graft, stent, stent-graft and web-stent that are made of a material having controlled heterogeneities along the blood flow or tissue-contacting surface of the stent.

BRIEF DESCRIPTION OF THE FIGURES

FIGS. 2A-2H are sequential cross-sectional fragmentary views illustrating device formation in accordance with the first embodiment.

FIGS. 8A-8G are sequential fragmentary cross-sectional views illustrating a fourth embodiment of a covered stent suitable for drug eluting applications made by the method of the making.

FIG. 16A is a top-plan view of a graft or web region with a plurality of openings passing there through.

FIG. 16B is a top plan view of an alternative embodiment of a graft or web region with a plurality of openings passing there through.

FIG. 16C is a top plan view of a third embodiment of a graft or web region with a plurality of openings passing there through.

DETAILED DESCRIPTION OF THE PREFERRED EMBODIMENTS

Figure 1:
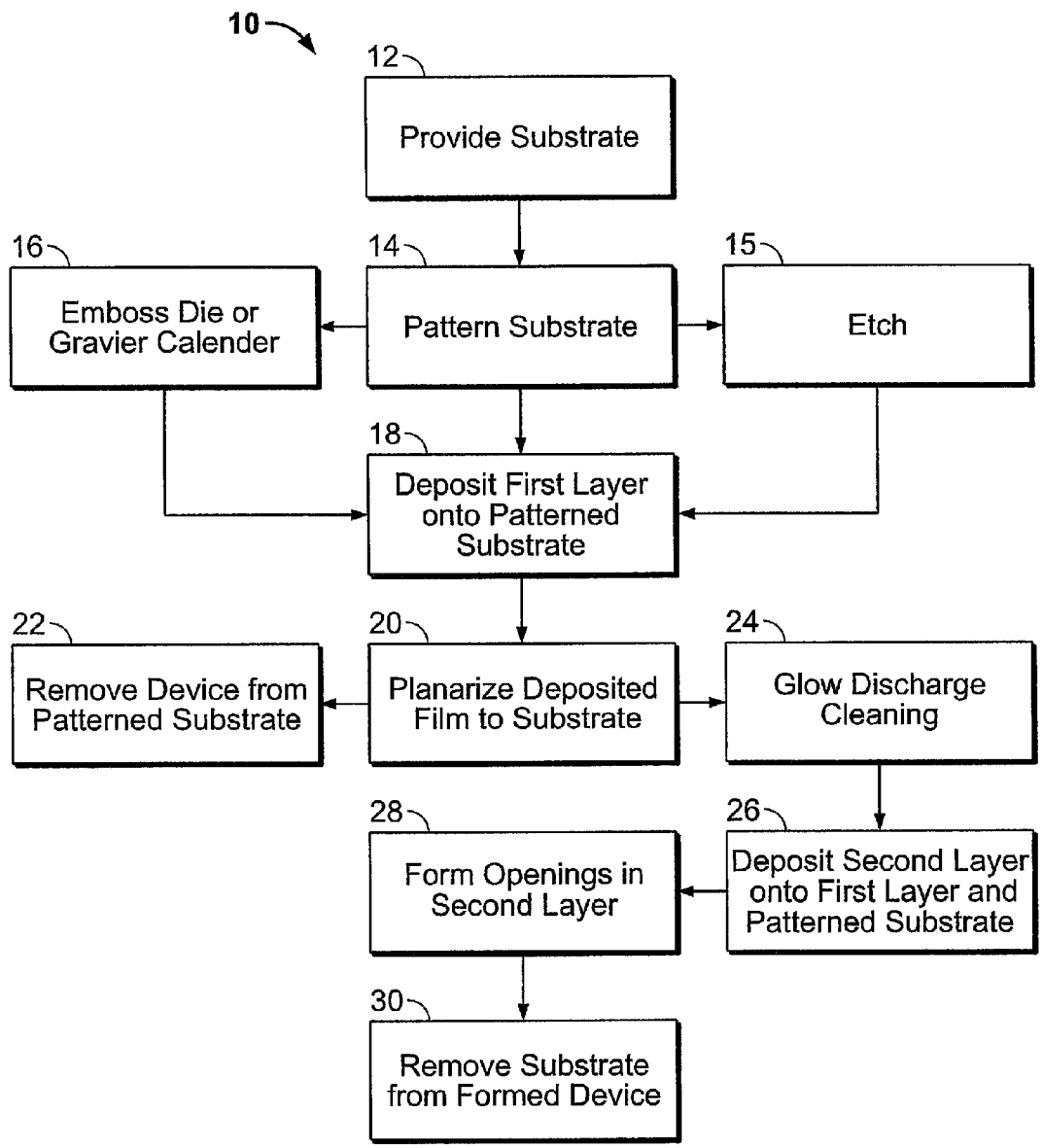
FIG. 1 is process diagram illustrating a first embodiment of the method of the present invention.

According to the present invention, alternative embodiments of a method for fabricating medical devices are disclosed and taught. Additionally, metallic or pseudometallic medical devices made by the inventive methods are disclosed and taught. While the invention is described with reference to certain preferred embodiments and examples, these are exemplary and are not meant to limit the scope of the invention.

Additionally, medical devices fabricated by the inventive methods are provided which preferably have surfaces thereof having heterogeneities which are controlled during the fabrication process by controlling the conditions of fabrication. The inventive medical devices may be made utilizing a pre-fabricated scaffold or cover, or a vacuum deposited scaffold or cover, either of which may originate in either a planar or cylindrical conformation. Where a scaffold is provided, either from a pre-fabricated scaffold or by vacuum deposition formation, the cover may be added to the scaffold by vacuum deposition. Alternatively, where a cover is provided, either by pre-fabrication or by vacuum deposition formation, then a scaffold may be added either by vacuum deposition or by imparting a pattern of support members to the film by removing at least some regions of the film to create thinner regions in the starting film and defining relatively thinner and thicker film regions, such as thinner web regions between adjacent structural scaffold members formed by thicker film regions and/or relatively thinner graft regions. An additive methodology may include vacuum deposition or lamination of a pattern of support members upon the planar or cylindrical film. A subtractive methodology includes etching unwanted regions of material by masking regions to form the structural scaffold members and expose unmasked regions to the etchant. Additionally, in order to improve in vivo healing, it is advantageous to impart openings passing through the web or the graft. The openings are preferably produced during the process of forming the web or the graft. The openings in the web or the graft may be formed by conventional methods such as photolithographic processes, by masking and etching techniques, by mechanical means, such as laser ablation, EDM, or micromachining, etc. Suitable deposition methodologies, as are known in the microelectronic and vacuum coating fabrication arts and incorporated herein by reference, are plasma deposition and physical vapor deposition which are utilized to impart a metal layer onto the stent pattern.

The implantable endoluminal devices are formed from at least one structural scaffold member, that serves as a scaffold and provides the requisite support for the device, and a metallic or pseudometallic thin film cover that covers at least a portion of the structural scaffold member. A plurality of openings are formed in the cover to impart flexibility and compliance to the cover, while serving to filter embolic material and permitting transmural cellular growth for implantable devices. The implantable endoluminal devices have sufficient longitudinal flexibility to traverse tortuous anatomical pathways without risk of injury and are deployable at a remote situs with the structural scaffold member providing support for the thin film cover to retain it either in a deployed position, such as in the case of an embolic filter, or affixed against a vascular wall or aneurysmal thrombus, such as in the case of a covered stent or supported graft.

Suitable deposition methodologies, as are known in the microelectronic and vacuum coating fabrication arts and incorporated herein by reference, are plasma deposition and physical vapor deposition. Of particular relevance are commonly assigned, published U.S. Patent Publication Nos. 2003/0028246 and 2003/0059640, which are hereby incorporated by reference and teach physical vapor deposition methods for fabricating metallic and pseudometallic materials suitable for fabricating medical devices.

In accordance with another aspect of the inventive medical device, it is contemplated that more than one cover members are employed, with an outer diameter of a first cover member being smaller than the inner diameter of a cover member, such that the first cover member is concentrically engageable within a lumen of the second cover member. Both the first and second cover members have a pattern of a plurality of openings passing there through. The first and second cover members are positioned concentrically with respect to one another, with the plurality of patterned openings being positioned out of phase relative to one another such as to create a tortuous cellular migration pathway through the wall of the concentrically engaged first and second cover members. In order to facilitate cellular migration through and healing of the first and second cover members in vivo, it is preferable to provide additional cellular migration pathways that communicate between the plurality of openings in the first and second cover members. These additional cellular migration pathways may be imparted as 1) a plurality of projections formed on either the luminal surface of the second cover or the abluminal surface of the first cover, or both, which serve as spacers and act to maintain an annular opening between the first and second cover members that permits cellular migration and cellular communication between the plurality of openings in the first and second graft members, or 2) a plurality of microgrooves, which may be random, radial, helical, or longitudinal relative to the longitudinal axis of the first and second cover members, the plurality of microgrooves being of a sufficient size to facilitate cellular migration and propagation along the groove without permitting fluid flow there through, the microgrooves serve as cellular migration conduits between the plurality of openings in the first and second graft members. Methods for forming such microgrooves and their utilization in promoting endothelialization are described more fully in commonly-assigned U.S. Pat. No. 6,190,404 issued Feb. 20, 2001 and in U.S. Patent Application Publication No. 20020017503 published Feb. 14, 2002, both of which are hereby expressly incorporated by reference.

A covered scaffold device in accordance with one embodiment may be forming or joining a cover member with a structural scaffold support member. Either or both of the cover member and the structural scaffold support member may be formed in accordance with the inventive methods or may be provided as pre-fabricated materials. A covered scaffold may be formed by first forming, such as by vacuum deposition methods or by etching a pre-existing material blank, a graft member as a contiguous thin sheet or tube which projects outwardly from at least one aspect of the plurality of structural scaffold members. The thin sheet is then everted over the structural scaffold members and brought into a position adjacent a terminal portion of the plurality of structural scaffold members such that it covers one or both of the putative luminal or abluminal surfaces of the plurality of structural scaffold members. The graft member is then mechanically joined at an opposing end, i.e., the putative proximal or the putative distal end of the plurality of structural scaffold members.

In accordance with one of the embodiments, there is provided a covered scaffold-supported device, termed a "web-stent" in which scaffold members provide a primary means of structural support for the webbed-stent device. The scaffold members may be arranged in any manner as is known in the art of stent or embolic filter fabrication, e.g., single element forming a circle or ellipse, a single or plural elements which form a tubular diamond-like or undulating pattern, in which adjacent structural scaffold members are spaced apart forming open regions or interstices between adjacent structural scaffold members. In one embodiment, the interstices or open regions between adjacent structural scaffold members are subtended by a cover material that is the same material or a material exhibiting similar biological and mechanical response as the material that forms the plurality of structural scaffold members. This cover may be formed within all or a portion of the interstitial area or open regions between the plurality of structural scaffold members and may either be integrally part of or connected to one or more structural scaffold members, or may overlay or may underlay a structural scaffold member.

Where a device is being fabricated, the thickness of the deposited or pre-fabricated starting film may be less than that where a web-stent is being formed, due to the absence of structural scaffold members in the graft member. However, where a stent-graft or a web-stent is being fabricated, structural scaffold members may be formed by alternative methods. The structural scaffold members may be formed by additive techniques by applying a pattern of structural scaffold members onto a film, such as by vacuum deposition techniques or conventional metal forming techniques, such as laminating or casting. Conversely, the structural scaffold members may be provided first, either by a deposition methodology or as a pre-fabricated structural scaffold; then the cover added to the scaffold by deposition or mechanical affixation. Subtractive or selective removal techniques may alternatively be employed to remove material from patterned regions on a film, such as by etching a pattern of interstitial regions between adjacent structural scaffold members until a thinner film is created which forms the web subtending the plurality of structural scaffold members. Where a pre-existing stent is employed as the structural scaffold members, obviously, the structural scaffold members do not need to be fabricated or formed.

In accordance with several embodiments, the graft, the plurality of structural scaffold members and the web are fabricated of the same or similar metals or metal-like materials. In order to improve healing response, it is preferable that the materials employed have substantially homogenous surface profiles at the blood or tissue contact surfaces thereof. A substantially homogeneous surface profile is achieved by controlling heterogeneities along the blood or tissue-contacting surface of the material. The heterogeneities that are controlled in accordance with an embodiment that include: grain size, grain phase, grain material composition, stent-material composition, and surface topography at the blood flow surface of the stent. Additionally, the embodiments provide methods of making endoluminal devices having controlled heterogeneities in the device material along the blood flow or tissue-contacting surface of the device. Material heterogeneities are preferably controlled by using conventional methods of vacuum deposition of materials onto a substrate.

The surface of a solid, homogeneous material can be conceptualized as having unsaturated inter-atomic and intermolecular bonds forming a reactive plane ready to interact with the environment. In practice, a perfectly clean surface is unattainable because of immediate adsorption of airborne species, upon exposure to ambient air, of O, $O_2$, $CO_2$, $SO_2$, NO, hydrocarbons and other more complex reactive molecules. Reaction with oxygen implies the formation of oxides on a metal surface, a self-limiting process, known as passivation. An oxidized surface is also reactive with air, by adsorbing simple, organic airborne compounds. Assuming the existence of bulk material of homogeneous subsurface and surface composition, oxygen and hydrocarbons may adsorb homogeneously. Therefore, further exposure to another environment, such as the vascular compartment, may be followed by a uniform biological response.

In accordance with an aspect of the embodiments, there is provided a vacuum deposited device that is fabricated of a material having surface material heterogeneities controlled during deposition of the material. Current manufacturing methods for fabricating endoluminal stents fail to achieve the desired material properties. As discussed above, stents are fabricated from bulk metals that are processed in a manner that incorporates processing aides to the base metal. Presently, stents are made from hypotubes formed from bulk metals, by machining a series of slots or patterns into the hyptotube to accommodate radial expansion, or by weaving wires into a mesh pattern.

The embodiments consists of a medical device, such as a scaffold supported cover or graft, which is made of a bulk material having controlled heterogeneities on a surface thereof. Heterogeneities are controlled by fabricating the bulk material of the stent to have defined grain sizes that yield areas or sites along the surface of the stent having optimal protein binding capability. The characteristically desirable properties of the inventive stent are: (a) optimum mechanical properties consistent with or exceeding regulatory approval criteria, (b) controlling discontinuities, such as cracking or pinholes, (c) a fatigue life of 400 MM cycles as measured by simulated accelerated testing, (d) corrosion resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

Controlling the surface profile of an endoluminal device is significant because blood protein interactions with surfaces of endoluminal devices appear to be the initial step in a chain of events leading to tissue incorporation of the intravascular device. The embodiments are based, in part, upon the relationship between surface energy of the material used to make the endoluminal device and protein adsorption at the surface of the endoluminal device. The present inventors have found that a relationship exists between surface free energy and protein adsorption on metals commonly used in fabrication of endoluminal devices. In addition, specific electrostatic forces resident on the surface of metal endoluminal stents have been found to influence blood interactions with the stent surface and the vascular wall.

In accordance with a preferred embodiment, the inventive devices have surface profiles which are achieved by fabricating the devices by the same metal deposition methodologies as are used and standard in the microelectronic and nanofabrication vacuum coating arts, and which are hereby incorporated by reference. In accordance with a preferred embodiment, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed in accordance with the methods of making the shape memory nickel-titanium alloys have been deposited having thicknesses between 0.5 μm and 200 μm which exhibit shape memory properties without the need for post-deposition annealing to shape-set the deposited material. With the sputtering technique, it is preferable to employ a cylindrical sputtering target, a single circumferential source that concentrically surrounds the substrate that is held in a coaxial position within the source.

Alternate deposition processes which may be employed to form the stent in accordance with several embodiments which include cathodic arc, laser ablation, and direct ion beam deposition. In the metal fabrication arts, the crystalline structure of the deposited film affects the mechanical properties of the deposited film. These mechanical properties of the deposited film may be modified by post-process treatment, such as by, for example, annealing.

Materials to make the inventive graft, stent-graft and webstent are chosen for their biocompatibility, mechanical properties, i.e., tensile strength, yield strength, and their ease of deposition include, without limitation, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt chromium alloy, nickel-titanium alloy and stainless steel.

During deposition various deposition conditions, such as the chamber pressure, the deposition pressure, the partial pressure of the process gases, the target temperature, voltage bias, target composition, and the deposition rate are controlled to optimize deposition of the desired species onto the substrate and yield desired physical and mechanical properties to the deposited material. As is known in the microelectronic fabrication, nanofabrication and vacuum coating arts, both the reactive and non-reactive gases are controlled and the inert or non-reactive gaseous species introduced into the deposition chamber are typically argon and nitrogen. The substrate may be either stationary or moveable; either rotated about its longitudinal axis, moved in an X-Y plane, planatarily or rotationally moved within the deposition chamber to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant structural supports, web-regions or graft, both in the context of spatial orientation of patterns of regions of relative thickness and thinness, such as by varying the thickness of the film over its length to impart different mechanical characteristics under different delivery, deployment or in vivo environmental conditions.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as carbon, aluminum or organic based materials, such as photoresists, may be deposited intermediate the substrate and the stent and the sacrificial layer removed by melting, chemical means, ablation, machining or other suitable means to free the stent from the substrate.

Those of ordinary skill in the art, will understand and appreciate that alternative methods of removing material from areas that form relatively thinner regions of the device may be employed. For example, in addition to chemical etching, relatively thinner regions may be formed by removing bulk material by ion milling, laser ablation, EDM, laser machine, electron beam lithography, reactive ion etching, sputtering or equivalent methods which are capable of reducing the thickness of the material in either the graft region or the interstitial web region between the structural scaffold members. Alternatively, the structural scaffold members may be added to the defined interstitial web or graft regions to form the device, or the interstitial web or graft regions may be added to pre-existing structural scaffold members. Additive methods that may be employed include conventional metal forming techniques, including laminating, plating, or casting.

Similarly, a wide variety of initial bulk material configurations may be employed, including a substantially planar sheet substrate, an arcuate substrate or a tubular substrate, which is then processed by either subtractive or additive techniques discussed above.

By forming the structural scaffold members, the interstitial web and/or the graft of an integral, monolithic material, both the circumferential or hoop strength of the resultant device, as well as the longitudinal or columnar strength of the device are enhanced over conventional stent-graft devices. Additional advantages of the embodiments, depending upon fabrication methods, may include: controlled homogeneity and/or heterogeneity of the material used to form the device by deposition methodologies, enhanced ability to control dimensional and mechanical characteristics of the device, the ability to fabricate complex device conformations, ability to pattern and control the porosity of the web and/or graft regions, and a monolithic one-piece construction of a device which yields a minimized device profile and cross-sectional area. The devices of the alternative embodiments have relatively thicker and thinner regions, in which the thinner regions permit radial collapse of the device for endoluminal delivery. The inventive device exhibits superior column strength that permits smaller introducer size and more readily facilitates deployment of the device.

In accordance with a preferred embodiment, the cover regions of the inventive devices have a plurality of openings which pass through the thickness of the cover material. Each of the plurality of openings is dimensioned to permit cellular migration through the opening without permitting blood leakage or seepage through the plurality of openings and to exclude embolic material from passing into the general circulation. Alternative, such as in the case of an embolic filter, the openings will be of sufficient size to permit blood flow therethrough but capture embolic material. The plurality of openings may be random or may be patterned. However, in order to control the effective porosity of the device, it is desirable to impart a pattern of openings in the material used to fabricate the inventive device.

With particular reference to FIG. 1, a first preferred embodiment of the inventive method 10 is illustrated. A substrate suitable for use in vacuum deposition is provided 12, and the substrate is patterned 14 with a pattern corresponding to a desired scaffold geometry. The pattern may be provided by any suitable method, such as etching 15, embossing using an embossing die or gravure calendaring 16. The scaffold may be formed by depositing a first material onto the patterned substrate 18 and into the patterning, then planarized 20 to the upper or outer surface of the substrate, leaving the first material layer present in the pattern of the substrate 18. In accordance with the preferred embodiments, the first material layer is preferably a biocompatible material, such as stainless steel or a shape memory material, such as nickel-titanium alloy or cobalt-chromium alloy; the material is preferably vacuum deposited by sputtering, but may also be deposited by evaporation, ion bombardment, chemical vapor deposition or electrochemical deposition. If desired, the formed scaffold may be removed from the substrate 22 and prepared for use as a medical scaffold material either alone or with a separately formed cover material. However, in accordance with the inventive method 10, it is preferred that the planarized substrate and deposited first material resident in the pattern on the substrate be cleaned, such as by glow discharge cleaning 24, then a second material be deposited onto the planarized first material and the substrate 26. A plurality of openings are then created which pass through the second material 28, preferably in regions which do not overly a scaffold member. At this point, the substrate may be removed from the formed device 30, such as by selective chemical etching.

FIGS. 2A-2H sequentially depict device formation by the foregoing described method 10. First a substrate 40 is provided which is suitable for vacuum deposition. In accordance with a most preferred embodiment, the substrate 40 is preferably a deoxygenated copper material which may have a titanium nitride coating on a surface thereof as a diffusion barrier to prevent migration of minute amounts of copper into the deposited layer. A patterning member 50, which may either by an embossing die or gravure plate, having pattern-forming regions 52 corresponding to a desired pattern for the scaffold, is engaged with the substrate 40 to create substrate pattern regions 42 in or on the substrate 40. Those skilled in the art will understand and appreciate that the pattern-forming regions 52 on the patterning member may correspond to either a positive or negative of the desired pattern for the scaffold, and hence, either consist of raised projections emanating from the surface of the patterning member 50 or consist of recesses formed in the surface of the patterning member 50. Depending upon whether the patterning member 50 is provided with a positive or negative pattern of the desired scaffold geometry, the corresponding negative or positive pattern of substrate pattern regions 42 will be formed in or on the substrate 40. For purposes of illustration only, patterning member 50 and pattern-forming regions 52 are shown as a positive pattern corresponding to the scaffold geometry.

Once the patterned substrate 40 is formed, a scaffold-forming material 44 is vacuum deposited onto the substrate 40. Scaffold-forming material 44 conforms to the substrate pattern regions 42 as shown in FIG. 2D. Where the substrate pattern regions 42 are recesses, as depicted in FIGS. 2B-2E, the scaffold-forming material 44 is preferably planarized to the surface of the substrate 40, leaving the scaffold-forming material 44 present only in the substrate pattern regions 42 and not on interstitial regions 45 between the scaffold 46 or on other regions of the substrate 40. At this point, the scaffold forming material 44 conforms to the desired scaffold geometry and the formed scaffold 46 may be released from the substrate 40, such as by selectively chemically etching the substrate 40. On the other hand, where the substrate pattern regions 42 are raised projections, interstitial regions 45 between adjacent members of the scaffold 46 may be removed by mechanical or thermal methods, such as laser ablation or electrical discharge machining (EDM).

In accordance with one embodiment, however, and as illustrated in FIGS. 2G and 2H, rather than removing the formed scaffold 46 from the substrate 40, it is desirable to leave the formed scaffold 46 in the substrate as depicted in FIG. 2E and vacuum deposit a cover material 48 onto the scaffold 46 and the substrate 40. In this manner, the deposited cover material 48 is deposited over both the scaffold 46 and the interstitial regions 45 on the substrate 40.

After the cover material 48 and the scaffold 46 are formed, and preferably while they remain on the substrate 40 for ease of handling, a plurality of openings 49 are formed which pass through the thickness of the cover material 48 in the interstitial regions 45. It is desirable, though not required, that the openings 49 are not formed in the cover material 48 in those areas which overlie the scaffold 46 so as not to impinge upon the scaffold 46. After the plurality of openings 49 are formed, the substrate 40 is selectively removed from the formed device, such as by selective chemical etching.

In accordance with the preferred embodiments, both the first material for the scaffold 46 and the cover material 48 are formed of biocompatible metals or pseudometals. The plurality of openings 49 may be random or may be patterned. It is preferable that the size of each of the plurality of openings 49 be such so as to exclude friable embolic material from passing through the openings 49, as well as to permit endothelialization to aid in healing of implantable devices.

In accordance with a further embodiment, a method for making a drug eluting device 105 is shown in FIGS. 8A-8G. The method for making a drug eluting device 105 entails substantially identical processing as formation of a covered scaffold described above with reference to FIGS. 1 and 2. A substrate 40 is patterned and layered with a scaffold-forming material 46 and a cover forming layer 48 is then deposited onto the scaffold-forming material 46. However in accordance with the method for making a drug eluting device 105, instead of removing the substrate from the formed covered scaffold, a second scaffold 110 is disposed on the cover-forming material 48, followed by deposition of a sacrificial material 112 onto the second scaffold 110 and the cover-forming material 48. The sacrificial material 112 is preferably planarized to expose upper surfaces of the second scaffold-forming material 110, then a second cover-forming material 114 is deposited onto the sacrificial material 112 and the second scaffold-forming material 110. A plurality of openings 116 may then be formed through the second cover-forming material 114, preferably in regions which do not overlie the second scaffold-forming material 110. The plurality of openings 16 may also be formed through the first cover-forming material 48 at the same time as those being formed through the second cover-forming material 114. The sacrificial material 112, may then be removed through the plurality of openings 16, such as by selective chemical etching, to leave a void plenum 120 intermediate the cover-forming material 48 and the second cover-forming material 114, which are maintained in spaced apart relationship by the second scaffold-forming material 110. The substrate 40 may be removed, preferably by selective chemical etching.

A pharmacologically active agent may then be loaded into the void plenums 120 by known methods, with known carriers or excipients, and with known matrices. Local or localized delivery of drug or drug combinations may be utilized to treat a wide variety of conditions utilizing any number of medical devices, or to enhance the function and/or life of the device. Accordingly, in addition to the embodiments described herein, therapeutic or pharmaceutical agents may be added to any component of the device, including within the void plenums 120, during fabrication to treat any number of conditions. In addition, therapeutic or pharmaceutical agents may be applied to the device, such as in the form of a drug or drug eluting layer, or surface treatment after the device has been formed. In a preferred embodiment, the therapeutic and pharmaceutical agents may include any one or more of the following: antiproliferative/antimitotic agents including natural products such as vinca alkaloids (i.e. vinblastine, vincristine, and vinorelbine), paclitaxel, epipidopodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) ll$_b$/lll$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

For such drugs the ideal pharmacokinetic profile will be one wherein the drug concentration reached therapeutic levels without exceeding the maximum tolerable dose and maintains these concentrations for extended periods of time until the desired therapeutic effect is reached. One of the ways such a profile can be achieved in an ideal case scenario would be by encapsulating the drug in a polymer matrix. The technology of polymeric drug delivery has been studied in details over the past 30 years and numerous excellent reviews are readily available to those skilled in the art. Polymeric drug delivery offers several advantages, including, for example: (1) Localized delivery of drug: The product can be implanted directly at the site where drug action is needed and hence systemic exposure of the drug can be reduced. This becomes especially important for toxic drugs which are related to various systemic side effects (such as the chemotherapeutic drugs). (2) Sustained delivery of drugs: The drug encapsulated is released over extended periods and hence eliminates the need for multiple injections. This feature can improve patient compliance especially for drugs for chronic indications, requiring frequent injections (such as for deficiency of certain proteins); (3) Stabilization of the drug: The polymer can protect the drug from the physiological environment and hence improve its stability in vivo. This particular feature makes this technology attractive for the delivery of labile drugs such as proteins.

The drug may be released from the polymer matrix either by diffusion out of the polymer matrix or by degradation of the polymer matrix of a combination of diffusion and degradation mechanisms. Polymer degradation may occur by enzymatic means, hydrolysis of a combination of these two. Hydrolysis, in turn, may be mediated by bulk erosion or by surface erosion of the polymer matrix. For a given drug, the release kinetics from the polymer matrix are predominantly governed by three factors, namely, the type of polymer, polymer morphology and the excipients present in the system.

The polymer could be non-degradable or degradable. A major disadvantage with non-degradable polymers is that a surgery may be required to harvest these polymers out of the body once they are depleted of the drug. Degradable polymers on the other hand do not require surgical intervention and hence are preferred for drug delivery applications. However, since they degrade to smaller absorbable molecules, it is important to make sure that the polymers are non-toxic in nature. Commonly employed polymers include, for example, polylactide (PLA), poly(lactide-co-glycolide) (PLGA), Poly (urethanes), Poly(siloxanes) or silicones, Poly(methyl methacrylate), Poly(vinyl alcohol), Poly(ethylene), Poly(vinyl pyrrolidone) and the specific polymers Poly(2-hydroxy ethyl methacrylate), Poly(N-vinyl pyrrolidone), Poly(methyl methacrylate), Poly(vinyl alcohol), Poly(acrylic acid), Polyacrylamide, Poly(ethylene-co-vinyl acetate), Poly(ethylene glycol), Poly(methacrylic acid).

Degradation of lactide based polymers and in general all hydrolytically degradable polymers, depends on the following properties: (1) chemical composition: The rate of degradation of polymers depends on the type of degradable bonds present on the polymer. In general, the rate of degradation of different chemical bonds follows as Anhydride>Esters>Amides; (2) crystallinity: generally, the higher the crystallinity of a polymer, the slower is its rate of degradation; and (3) hydrophilicity: if the polymer has a lot of hydrophobic groups present on it, then it is likely to degrade slower than a polymer which is hydrophilic in nature. Polylactides are known to be more hydrophobic as compared to PLGA and take a longer time to degrade. Among the polylactides, DL-PLA, which is a polymer of D and L-lactide, degrades faster than L-PLA, which is a homopolymer of L-lactide, presumably due to lesser crystallinity. Similarly, the more hydrophobic end-capped PLGA polymers degrade faster than the carboxyl-ended PLGA. Some new polymers showing promise as drug-delivery mechanisms include polyothroesters, polyphosphazenes, polyanhydrides and polyphosphoesters.

Morphology of the polymer matrix also plays an important role in governing the release characteristics of the encapsulated drug. The polymer matrix could be formulated as either micro/nano-spheres, gel, film or an extruded shape (such as cylinder, rod etc). The shape of the extruded polymer can be important to the drug release kinetics. For example, it has been shown that zero order drug release can be achieved using a hemispherical polymer form. Polymer microspheres are the most popular form due to manufacturing advantages as well as ease of administration (injectability by suspending in a vehicle). Polymer microspheres can be manufactured by using various techniques such as spray drying, solvent evaporation, etc. The type of technique used affects factors such as porosity, size distribution and surface morphology of the microspheres and may subsequently affect the performance of the drug delivery product.

Polymeric drug delivery products can be formulated with excipients added to the polymer matrix. The main objective of having excipients in the polymer matrix could be either to modulate the drug release, or to stabilize the drug or to modulate the polymer degradation kinetics. By incorporating basic salts as excipients in polymeric microspheres, the stability of the incorporated protein can be improved. It has been shown that these basic salts also slow the degradation of the polymer. Similarly, hydrophilic excipients can accelerate the release of drugs, though they may also increase the initial burst effect.

Figure 3:
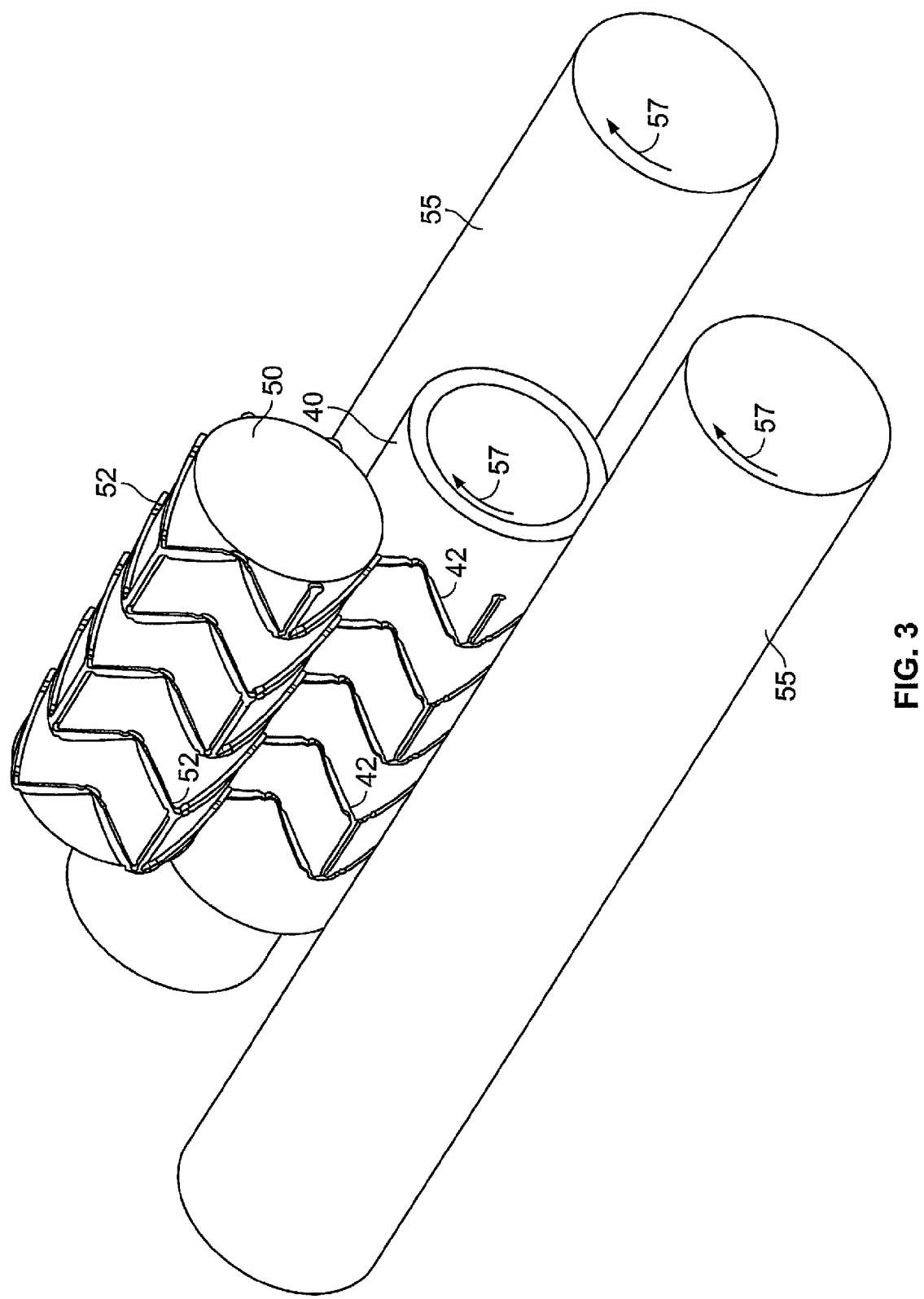
FIG. 3 is a diagrammatic representation of a gravure calendaring die engaged upon a substrate creating a corresponding pattern in the substrate.
Figure 4:
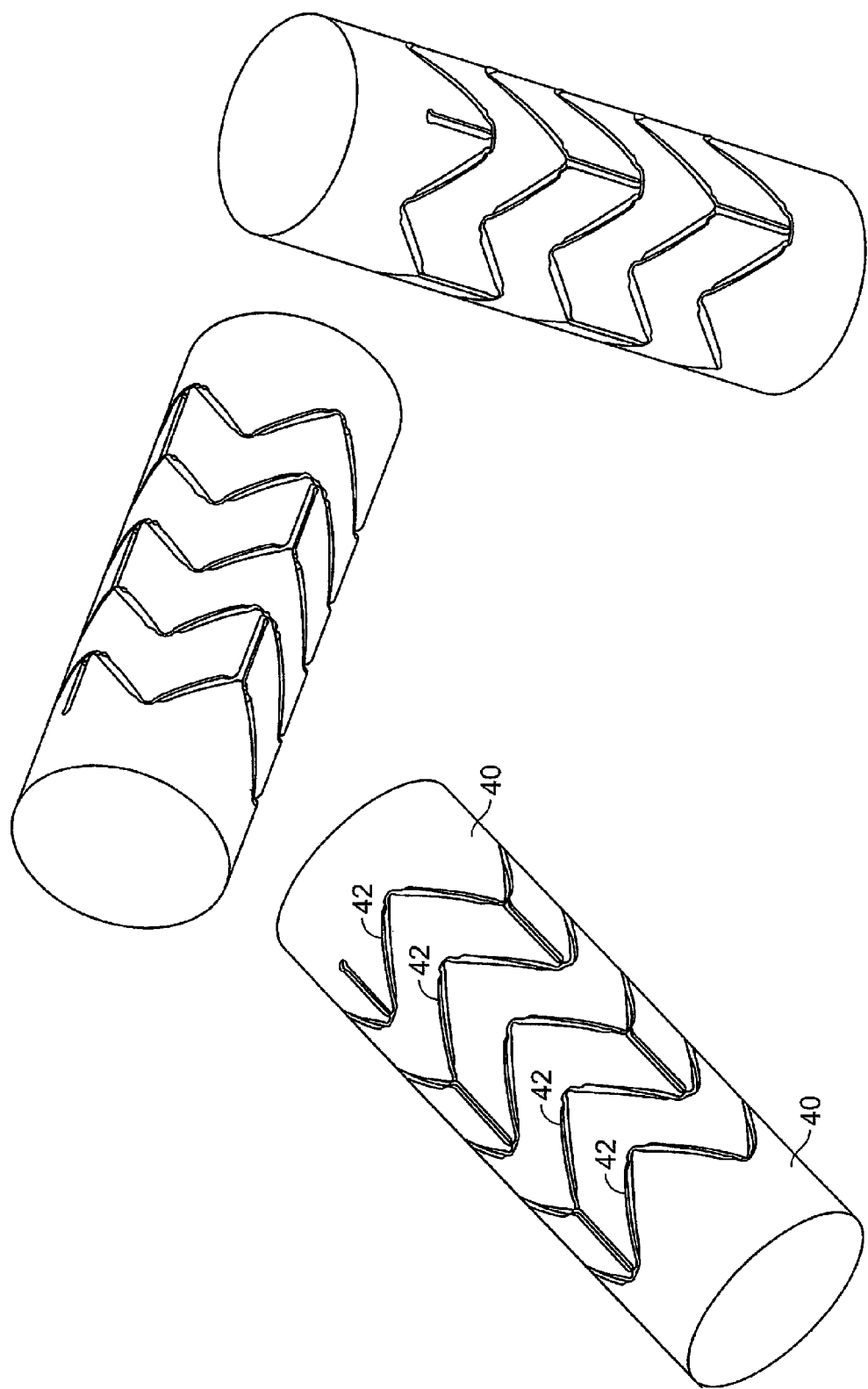
FIG. 4 is a perspective view of a gravure embossed substrate having a recessed pattern corresponding to a stent geometry.
Figure 5A:
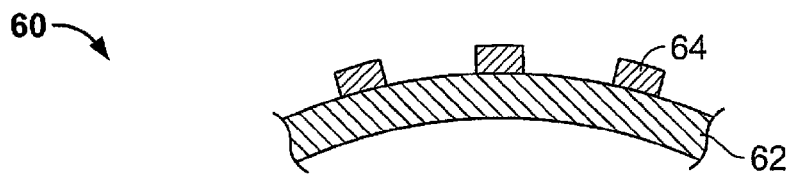
FIGS. 5A-5E are sequential cross-sectional fragmentary views illustrating device formation in accordance with a second embodiment.
Figure 5B:
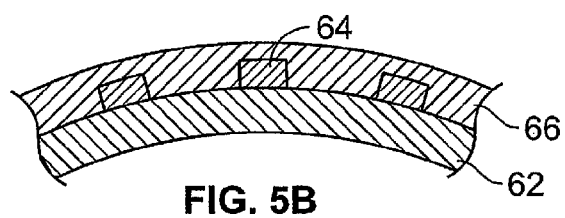
Figure 5C:
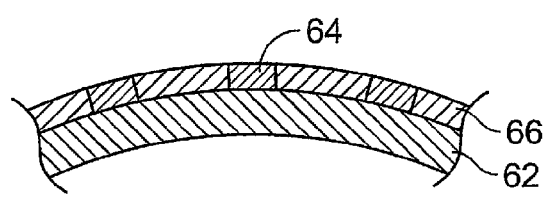
Figure 5D:
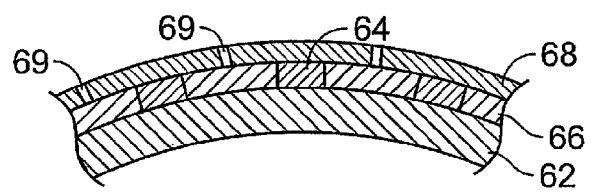
Figure 5E:
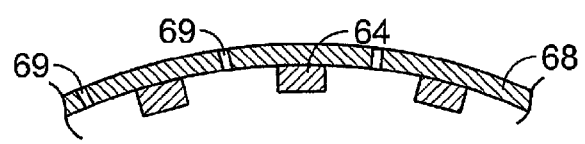
Figure 6:
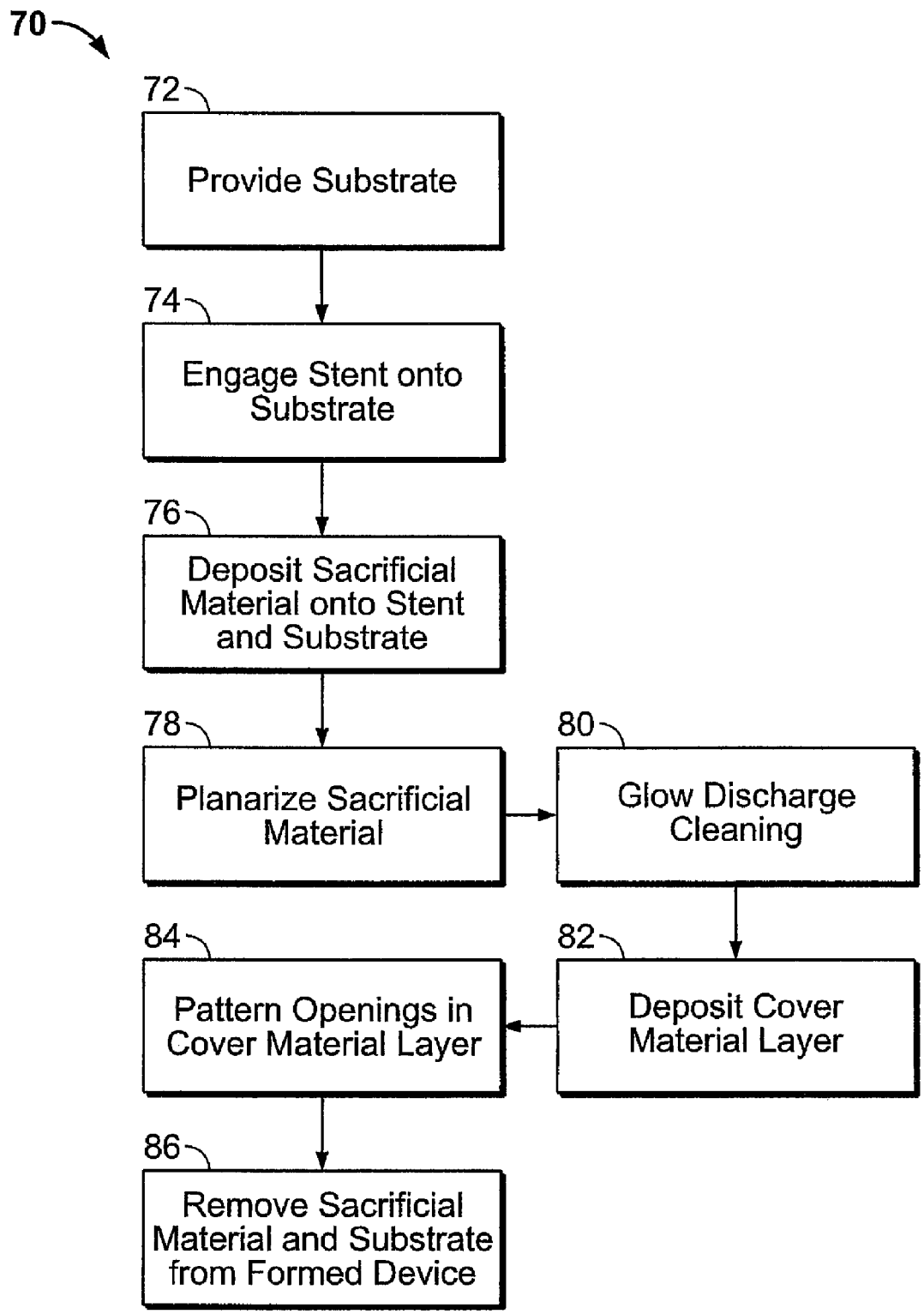
FIG. 6 is a process diagram illustrating the second embodiment of the method of making.

FIG. 3 depicts a prototypical system for imparting a scaffold pattern onto a cylindrical or tubular substrate 40. The resulting substrate 40 having the scaffold pattern 42 is shown in FIG. 4. An die 50 which carries a pattern 52 corresponding to the desired geometry of the scaffold 46 is provided. The substrate 40 is placed on a pair of cylindrical rollers 55, which impart a rotary movement 57 to the substrate 40 along its longitudinal axis. Contacting the die 50 with the surface of the substrate under pressure, causes the transfer of the pattern 52 from the die 50 to impart the corresponding pattern 42 on the substrate 40. While pattern 52 is shown as a positive pattern and, corresponding pattern 42 is shown as a negative pattern, pattern 52 and its corresponding pattern 42 may be negative-positive or positive-negative, as desired, depending upon the desired manner of fabricating the medical device. Where die 50 is an embossing die, it will be necessary that substrate 40 be fabricated of a material capable of being deformed under pressure to precisely accept and retain an embossed pattern in the surface thereof. Where die 50 is a gravure die, the pattern 52 is typically etched into the surface of the die 50, then a lithographic material is applied to the pattern 52 and transferred to the substrate 40. Gravure processes are typically used in photolithography to pattern the substrate 40.

FIGS. 5A-E and 6 illustrates an alternate embodiment of the inventive method 70 of making a covered scaffold device 60. Unlike method 10, according to method 70 a substrate is selected at step 72, then a pre-existing scaffold 64 is mounted onto a deposition substrate 62 at step 74. In this manner, the substrate 62 does not require patterning and a first step of depositing a scaffold-forming material is, similarly, not required. Once the scaffold 64 is mounted on the deposition substrate 62, a sacrificial material 66 is deposited over the scaffold 64 and the substrate 62 at step 76. The sacrificial material 66 is then planarized at step 78 to expose at least a top surface of the scaffold 64, while leaving remaining regions of the sacrificial material 66 covering the substrate 62 in interstitial regions of the scaffold 64. It is preferable to clean the planarized sacrificial material and exposed scaffold surface, such as by glow discharge cleaning, at step 80, before further processing. A cover material 68 is then deposited onto the exposed surfaces of the scaffold 64 and the sacrificial material 66 at step 82. Then, a plurality of openings are formed in the cover material 84, at step 84, through the deposited cover material 68 and into the sacrificial material 66, preferably in regions of the cover material 68 which do not overlay the scaffold 64 members. Finally, the substrate and the sacrificial material are removed at step 86, such as by selective chemical etching, to release the formed covered scaffold in FIG. 5E having a cover member 68 integrally joined to the scaffold 64.

Figure 7A:
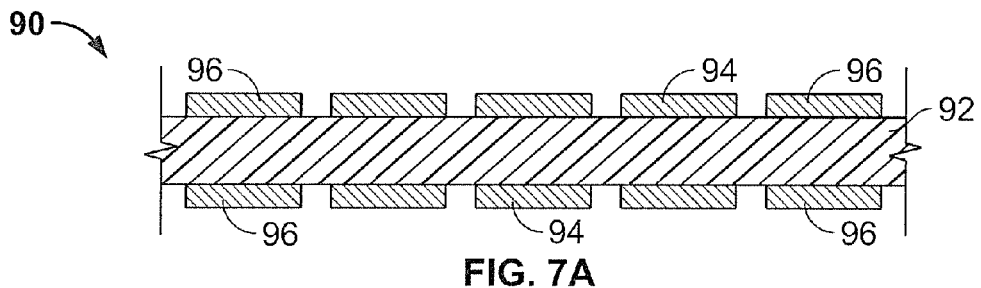
FIGS. 7A-7E are sequential cross-sectional views illustrating a third embodiment of an inventive covered stent made in accordance with the second embodiment of the method of making.
Figure 7B:
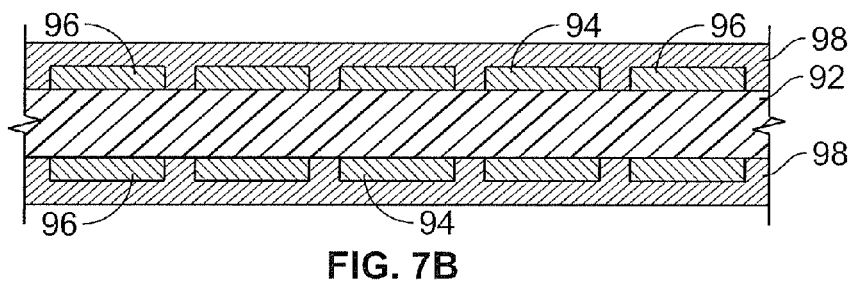
Figure 7C:
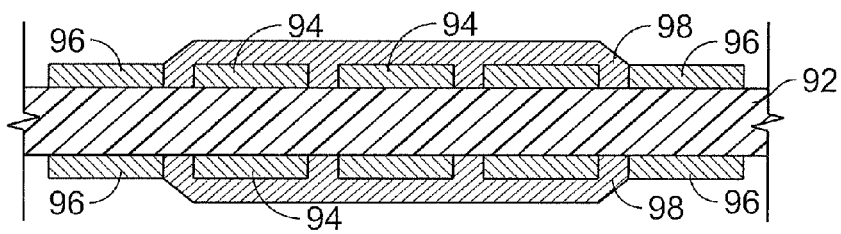
Figure 7D:
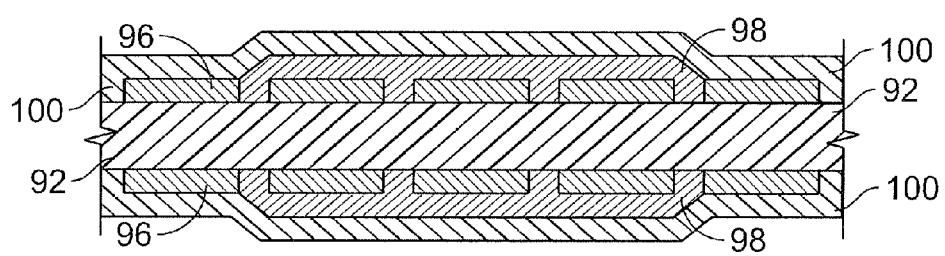
Figure 7E:
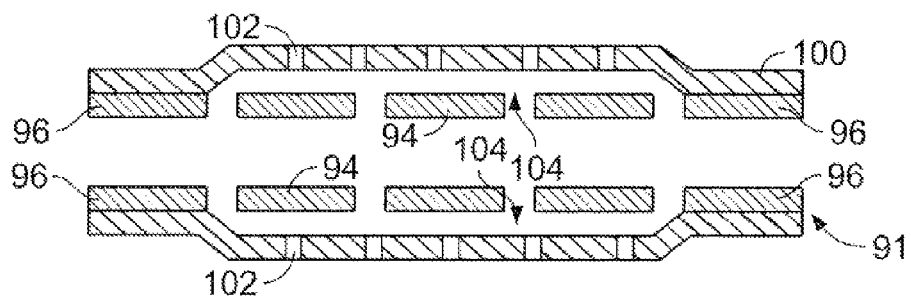

FIGS. 7A-E illustrate another alternative embodiment in which there is illustrated a method 90 for fabricating an inventive covered scaffold device consisting of a scaffold 94 and a cover 100 in which the cover 100 is integrally formed to only sections 96 of the scaffold 94. Covered scaffold device 91 is preferably fabricated by either forming the scaffold 94 as depicted in FIGS. 2A-2F, or by engaging a pre-existing scaffold 94 onto a deposition substrate 92 as depicted in FIG. 7A. A sacrificial material 98 is then deposited onto the scaffold 94 and substrate 92 as illustrated in FIG. 7B. The sacrificial material 98 is then planarized or otherwise removed to expose only portions 96 of the underlying scaffold 94. In accordance with a preferred embodiment, the scaffold 94 is a stent and the exposed portions 96 are situated at proximal and/or distal ends of the stent. By exposing only portions 96 of the scaffold 94 underlying the sacrificial material 98, other portions of the scaffold 94 remain covered by the sacrificial material 98. Subsequent deposition of a cover material 100 onto the exposed scaffold 94 portions 96 and the sacrificial material 98, integrally joins the exposed portions 96 of the scaffold 94 with the cover material, while the sacrificial material 98 maintains separation between the remaining regions of scaffold 94 underlying the sacrificial material 98 and the cover material 100, as illustrated in FIG. 7D. A plurality of openings 102 are formed in the cover material 100, preferably in those regions in which the cover material 100 overlays the sacrificial material 98, so as not to impinge upon or damage the underlying scaffold portions 96. It is anticipated, however, that the plurality of openings 100 may, however, be patterned on top of the scaffold 96 patterned where sacrificial material 98 is between the scaffold and cover material, and may patterned where the cover material 100 is directly on top of the scaffold 96 if the scaffold surface is sufficiently large without deleterious effects to the scaffold. After removal of the substrate 92 and the sacrificial material 98, the cover material 100 remains integrally joined only to the scaffold 94 portions 96, while remaining regions of the scaffold 94 are unjoined to the cover material 100 creating an open region 104 between the scaffold 94 and the cover material 100 which serves as a slip plane for expansion and relative movement of the scaffold 94 and the cover material 100.

The alternative embodiments comprise a medical device fabricated of a bulk material having controlled heterogeneities on a blood or tissue contacting surface thereof. Heterogeneities are controlled by fabricating the bulk material of the stent to have defined grain sizes that yield areas or sites along the surface of the stent having optimal protein binding capability. The characteristically desirable properties of the inventive stent are: (a) optimum mechanical properties consistent with or exceeding regulatory approval criteria, (b) controlling discontinuities, such as cracking or pinholes, (c) a fatigue life of 400 MM cycles as measured by simulated accelerated testing, (d) corrosion resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

Controlling the surface profile of an endoluminal device is significant because blood protein interactions with surfaces of endoluminal devices appear to be the initial step in a chain of events leading to tissue incorporation of the intravascular device. The alternative embodiments are based, in part, upon the relationship between surface energy of the material used to make the endoluminal device and protein adsorption at the surface of the endoluminal device. The present inventors have found that a relationship exists between surface free energy and protein adsorption on metals commonly used in fabrication of endoluminal devices. In addition, specific electrostatic forces resident on the surface of metal endoluminal stents have been found to influence blood interactions with the stent surface and the vascular wall.

In accordance with a preferred embodiment, the inventive grafts, stent-grafts and web-stents have surface profiles which are achieved by fabricating the graft, stent-graft and web-stent by the same metal deposition methodologies as are used and standard in the microelectronic and nano-fabrication vacuum coating arts, and which are hereby incorporated by reference. In accordance with a preferred embodiment, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source.

Alternate deposition processes which may be employed to form the stent in accordance with the alternative embodiments are cathodic arc, laser ablation, and direct ion beam deposition. As known in the metal fabrication arts, the crystalline structure of the deposited film affects the mechanical properties of the deposited film. These mechanical properties of the deposited film may be modified by post-process treatment, such as by, for example, annealing.

Materials to make the inventive graft, stent-graft and web-stent are chosen for their biocompatibility, mechanical properties, i.e., tensile strength, yield strength, and their ease of deposition include, without limitation, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

During deposition, the deposition process parameters, such as chamber pressure, deposition pressure, partial pressure of the process gases, the target temperature, bias voltage, substrate or source movement relative to the target, and power are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable; either rotated about its longitudinal axis, moved in an X-Y plane, planatarily or rotationally moved within the deposition chamber to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant structural supports, web-regions or graft, both in the context of spatial orientation of patterns of regions of relative thickness and thinness, such as by varying the thickness of the film over its length to impart different mechanical characteristics under different delivery, deployment or in vivo environmental conditions.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as carbon, aluminum or organic based materials, such as photoresists, may be deposited intermediate the substrate and the stent and the sacrificial layer removed by melting, chemical means, ablation, machining or other suitable means to free the stent from the substrate.

The resulting device may then be subjected to post-deposition processing to modify the crystalline structure, such as by annealing, or to modify the surface topography, such as by etching to expose a heterogeneous surface of the device.

Figure 9:
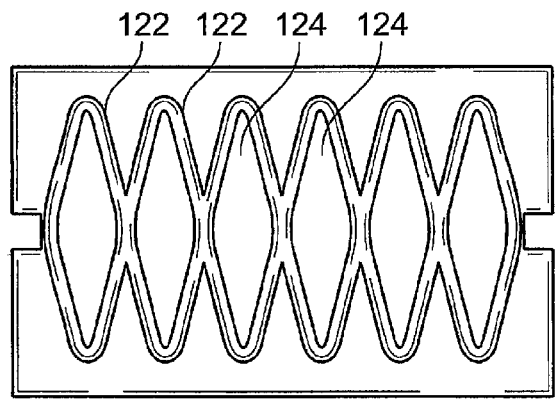
FIG. 9 is a photographic top plan view of a web-stent in accordance with one embodiment.
Figure 10:
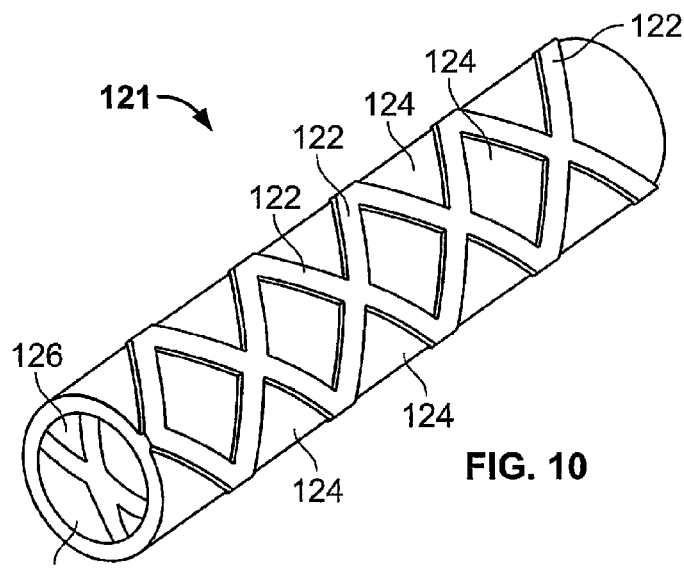
FIG. 10 is a perspective view of a preferred embodiment of the web-stent.

FIGS. 9 and 10 illustrate a web-stent 121 in accordance with one embodiment. The web-stent 121 is formed of a material blank, which has been either pre-manufactured or has been vacuum deposited as a planar or cylindrical film. The web-stent 121 is formed by masking regions of the material blank which are to form a plurality of structural scaffold members 122, and then etching the unmasked regions which then form interstitial webs 124 which subtend interstitial regions between adjacent structural scaffold members 122. The interstitial webs 124 are etched to a material thickness that is less than the thickness of the plurality of structural scaffold members 122. It is preferable to impart a plurality of openings in the interstitial webs 124 in order to permit endothelialization of the luminal surface 126 of the interstitial webs 124. The openings may be imparted as a random pattern or as a regular pattern in the interstitial web 124, as will be discussed hereinafter.

Figure 11:
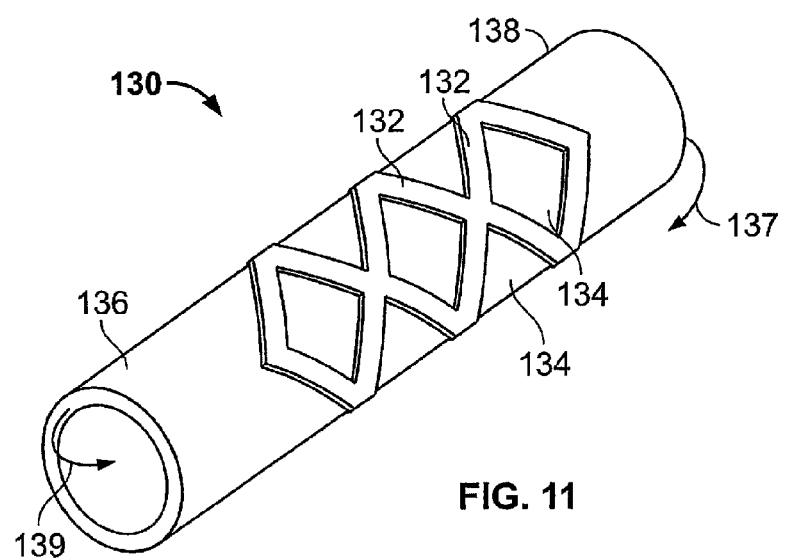
FIG. 11 is a perspective view of a stent-graft in accordance with one embodiment.

With reference to FIG. 11 there is depicted a covered scaffold 130 in accordance with one embodiment. Covered scaffold 130 is formed either from a tubular or planar material blank, which is etched to form the plurality of structural scaffold members 132 and interstitial regions 134 between the structural scaffold members 132. In addition, either or both a proximal 136 or a distal 138 cover region of the scaffold are provided and project outwardly from terminal structural scaffold members 132. The proximal graft region 136 and the distal graft region 138 are preferably etched to a reduced thickness of less than the thickness of the structural scaffold members, and are made with openings passing therethrough which promote cellular migration and exclude embolic material.

Under certain applications it may be useful to employ the covered scaffold 130 with either or both of the proximal 136 or distal 138 graft regions projecting outwardly from the structural supports 132 (FIG. 11).

Figure 12:
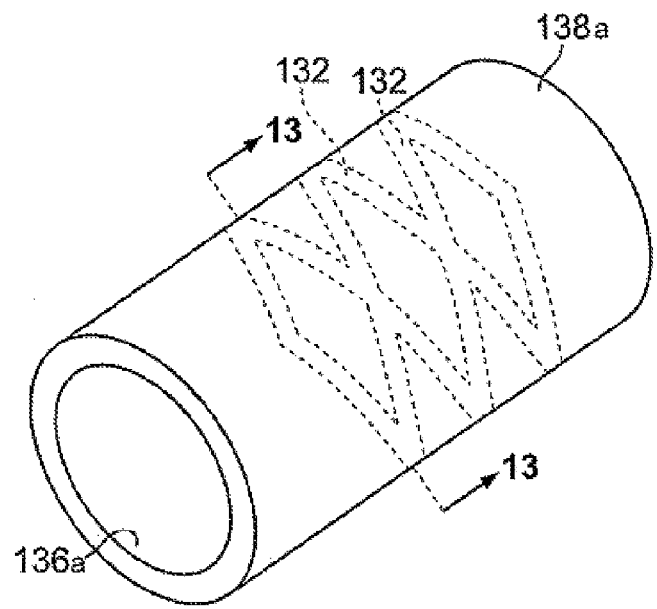
FIG. 12 is a perspective view of an alternative embodiment of the inventive stent-graft.
Figure 13:
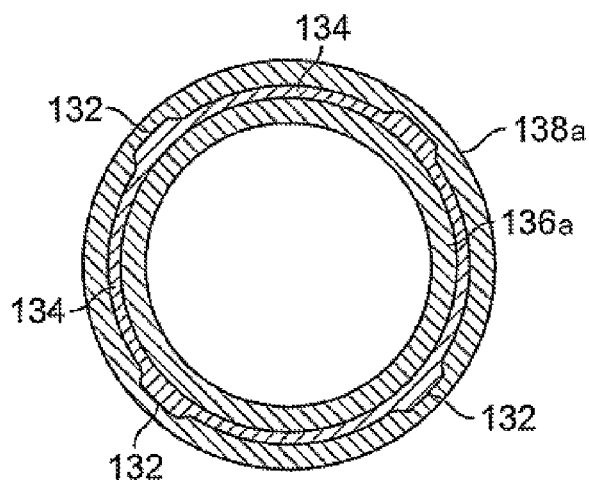
FIG. 13 is a cross-sectional view taken along line 13-13 of FIG. 12.

An alternative embodiment is illustrated in FIGS. 12 and 13. The alternative embodiment of the covered scaffold 130 involves covering the luminal and/or abluminal surfaces of a plurality of structural supports 132 with a luminal cover 136a and an abluminal cover 138a. The luminal cover 136a may initially be formed as the proximal graft region 136 in FIG. 11 and be luminally inverted 139 and passed into the lumen defined by the structural scaffold members 132. The abluminal cover 138a may initially be formed as the distal cover region 138 in FIG. 11 and be abluminally everted 137 over the structural scaffold members 132. Alternatively, the luminal cover 136a and the abluminal cover 138a may be formed as either pre-fabricated discrete cover members made of biocompatible metal or metal-like materials that engaged about the plurality of structural scaffold members 132. Portions of each of the abluminal cover 138a and the luminal cover 136a are mechanically joined to the plurality of structural scaffold members 132 or to one another, thereby effectively encapsulating the plurality of structural scaffold members 132 between the luminal cover 136a and the abluminal cover 138a. It is preferable that opposing free ends of each of the abluminal cover 138a and luminal cover 136a be joined to and co-terminus with a terminal portion of the plurality of structural scaffold members 132. Joining may be by mechanical means, such as welding, suturing, adhesive bonding, soldering, thermobonding, riveting, crimping, or dovetailing, or by deposition, such as by vacuum deposition, chemical vapor deposition or electrochemical deposition. In accordance with an alternate embodiment, the interstitial regions may be subtended by a web 134, as discussed hereinabove, with reference to FIGS. 9 and 10.

Those of ordinary skill in the art, will understand and appreciate that alternative methods of removing material from areas that form relatively thinner regions of the stent, web-stent or stent-graft may be employed. For example, in addition to chemical etching, relatively thinner regions may be formed by removing bulk material by ion milling, laser ablation, EDM, laser machine, electron beam lithography, reactive ion etching, sputtering or equivalent methods which are capable of reducing the thickness of the material in either the graft region or the interstitial web region between the structural scaffold members. Alternatively, the structural scaffold members may be added to the defined interstitial web or graft regions to form the device, or the interstitial web or graft regions may be added to pre-existing structural scaffold members. Additive methods that may be employed include conventional metal forming techniques, including laminating, plating, or casting.

Similarly, a wide variety of initial bulk material configurations may be employed, including a substantially planar sheet substrate, an arcuate substrate or a tubular substrate, which is then processed by either subtractive or additive techniques discussed above.

By forming the structural scaffold members, the interstitial web and/or the graft of an integral, monolithic material, both the circumferential or hoop strength of the resultant device, as well as the longitudinal or columnar strength of the device are enhanced over conventional stent-graft devices. Additional advantages of the alternative embodiments, depending upon fabrication methods, may include: controlled homogeneity and/or heterogeneity of the material used to form the device by deposition methodologies, enhanced ability to control dimensional and mechanical characteristics of the device, the ability to fabricate complex device conformations, ability to pattern and control the porosity of the web and/or graft regions, and a monolithic one-piece construction of a device which yields a minimized device profile and cross-sectional area. The devices of the alternative embodiments have relatively thicker and thinner regions, in which the thinner regions permit radial collapse of the device for endoluminal delivery. The inventive device exhibits superior column strength that permits smaller introducer size and more readily facilitates deployment of the device.

Figure 14:
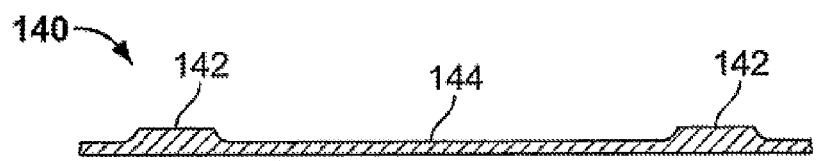
FIG. 14 is a cross-sectional view illustrating a pair of support members and a section of interstitial web between adjacent supporting members.
Figure 15:
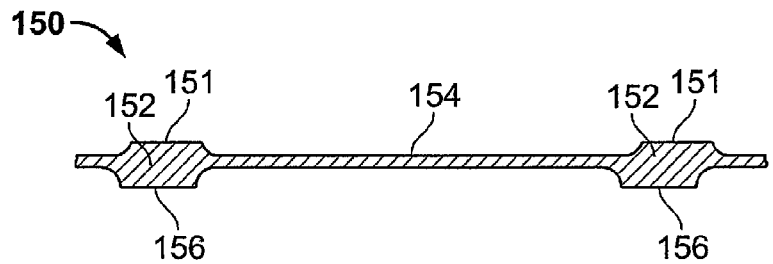
FIG. 15 is a cross-sectional view illustrating a pair of support members and a section of interstitial web between adjacent supporting members in accordance with an alternative embodiment.

As illustrated in FIGS. 14 and 15, the web and/or cover regions, 144, 154 between adjacent structural scaffold members 142, 152 may be co-planar with either the luminal or abluminal surface of the structural scaffold members 142, or may be positioned intermediate the luminal 151 and abluminal 156 surfaces of the structural scaffold members 152.

In accordance with a preferred embodiment, the web regions of the inventive web-stent, the graft regions of the inventive stent-graft and the inventive graft have a plurality of openings which pass through the thickness of the material used to fabricated the inventive devices. Each of the plurality of openings is dimensioned to permit cellular migration through the opening without permitting blood leakage or seepage through the plurality of openings. The plurality of openings may be random or may be patterned. However, in order to control the effective porosity of the device, it is desirable to impart a pattern of openings in the material used to fabricate the inventive device.

Figure 16A:
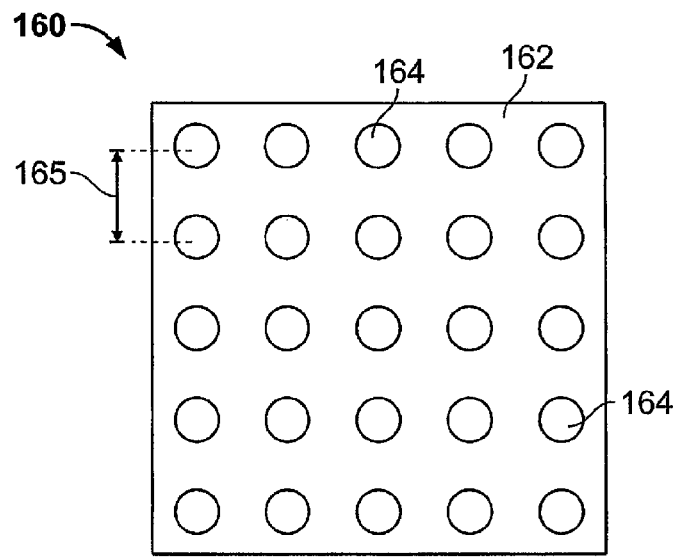
Figure 16B:
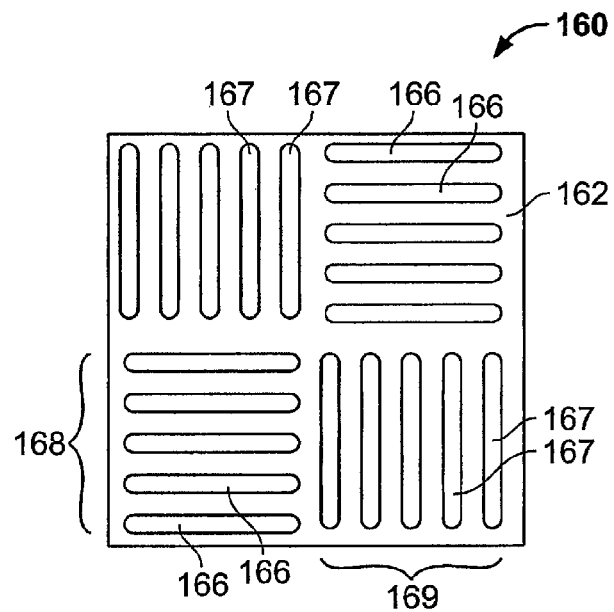
Figure 16C:
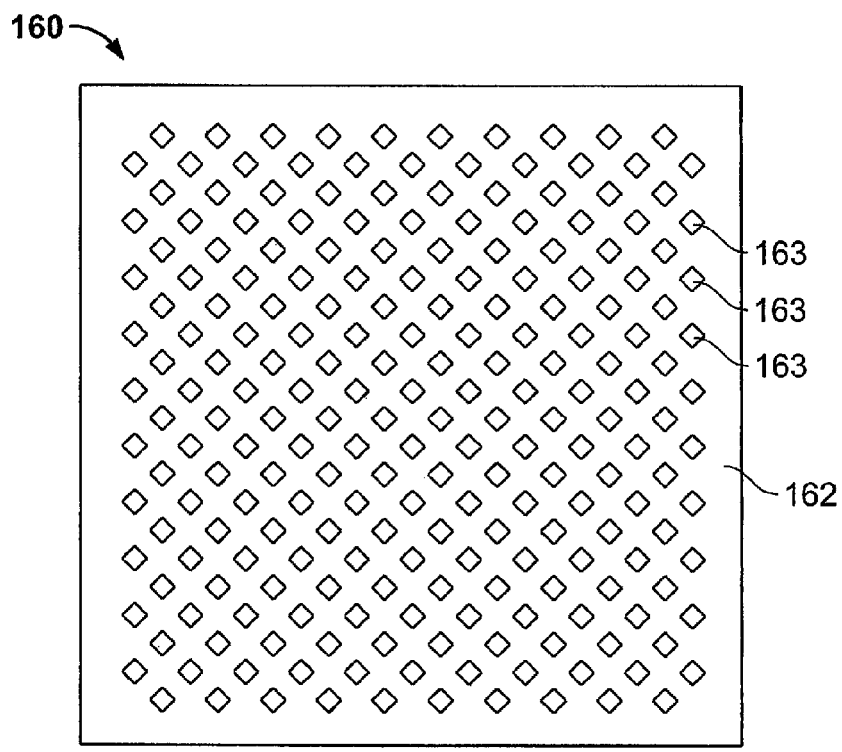

FIGS. 16A-16C depict several non-limiting examples of patterned openings in a section of material used to make the inventive covered scaffold devices in accordance with one embodiment. FIG. 16A depicts a material 160 with a plurality of circular openings 164 passing through the material substrate 162. The plurality of circular openings is patterned in a regular array of rows and columns with regular inter-opening spacing 165 between adjacent openings. In the particular embodiment illustrated the diameter of each of the plurality of openings is about 19 µm, with an inter-opening spacing in each row and column of about 34 µm on center. The thickness of the material 162 is preferably between about 0.5 µm and about 10 µm. FIG. 16B illustrates another example of a pattern of a plurality of openings useful in the alternative embodiments. The material 162 has a plurality of openings 166 and 167 passing there through. The pattern of the plurality of openings 166 and 167 is an alternating slot pattern in which the plurality of openings 166 are arrayed adjacent one another forming a y-axis oriented array 168 relative to the material 162, while a plurality of openings 167 are arrayed adjacent one another forming an x-axis oriented array 169 relative to the material 162. The y-axis-oriented array 168 and the x-axis-oriented array 169 are then positioned adjacent one another in the material 162. In this particular example, the inter-array spacing between the y-axis-oriented array 168 and the x-axis-oriented array 169 is about 17 µm, while each of the plurality of openings has a length of about 153 µm and a width of about 17 µm. An alternative design for the plurality of openings 167 and 166 is to orient all of the openings such that each slot opening has a longitudinal axis oriented along a common axis as the other slot openings. In this manner, the openings 167 and 166 may all be oriented along either the longitudinal axis or circumferential axis of the cover material 160. Finally, FIG. 16C illustrates a material 160 in which the material substrate 162 has a regular array of a plurality of diamond-shaped openings 163 passing through the material substrate 162. As with the alternative embodiments exemplified in FIGS. 16A and 16B, the dimension of the plurality of diamond-shaped openings 163 is of sufficient size to permit cellular migration through the openings 163, while preventing blood flow or seepage, and the passage of embolic material through the plurality of openings 163.

Figure 17A:
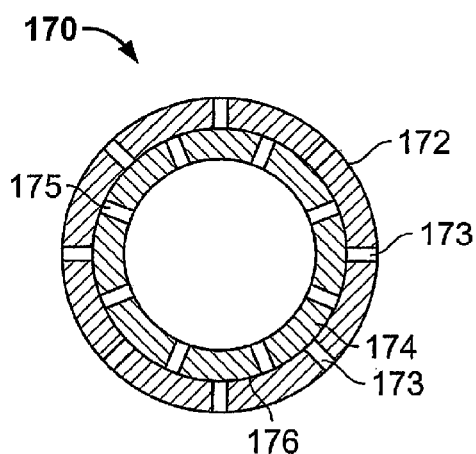
FIG. 17A is a transverse cross-sectional view of a first embodiment of a graft member in accordance with one embodiment; and 17B is a transverse cross-sectional view of a second embodiment of a graft member in accordance with one embodiment.
Figure 17B:
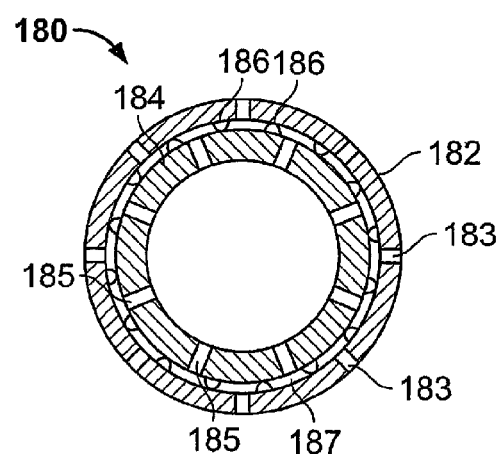

FIGS. 17A and 17B illustrate alternate preferred embodiments of graft 170 and graft 180 in accordance with one embodiment. Graft 170 consists generally of concentrically positioned luminal graft member 174 and abluminal graft member 172 and an interfacial region 176 where the luminal surface of the abluminal graft member 172 and the abluminal surface of the luminal graft member 174 are in immediate juxtaposition with one another. Both the luminal 174 and the abluminal 172 graft members are fabricated in accordance with the methodologies described above, and are provided with a plurality of patterned openings 173 in the abluminal graft member 172 and a plurality of patterned openings 175 in the luminal graft member 174. The plurality of patterned openings 173 and 175 are positioned out of phase relative to one another. By positioning the plurality of patterned openings 173 and 175 in an out-of-phase relationship, there is no continuous opening that passes through the interfacial region 176 which would permit blood flow or seepage from the lumen of the graft. However, in order to permit cellular migration from the abluminal surface of the graft to the lumen of the graft, the interfacial region 176 should have microroughness [not shown] which is oriented either randomly or selectively, such as helically or circumferential, about the interfacial region 176. The microroughness preferably has a peak-to-valley depth of between about 5 µm to about 65 µm most preferably between about 10 µm to 15 µm, may be either on the luminal surface of the abluminal graft 172 or on the abluminal surface of the luminal graft 174, or both. The microroughness spans the surface area region between adjacent pairs of openings 173, 175, and the microroughness depth permits cellular migration across the surfaces between adjacent openings 173 and 175. The microroughness is not large enough to permit fluid passage through the inter-opening regions at the interface 176 between the luminal graft 174 and the abluminal graft 172. This property of permitting cellular growth is similar to the difference between the porosity of expanded polytetrafluoroethylene grafts which do not require pre-clotting, and the much larger porosity of polyester or DACRON grafts which require pre-clotting to prevent fluid seepage there from.

FIG. 17B illustrates an alternative embodiment of the inventive graft 180 in which an abluminal graft member 182 is concentrically positioned about a luminal graft member 184. Each of the abluminal graft member 182 and the luminal graft member 184 having a plurality of patterned openings 183, 185, respectively, passing there through. As with the embodiment depicted in FIG. 17A, the plurality of patterned openings 183 and 185 are positioned in an out-of-phase relationship to one another in order to prevent forming a continuous opening between the luminal and abluminal surfaces of the graft 180. However, unlike the embodiment in FIG. 17A, there is no corresponding interfacial region 176. Rather, an annular open region 187 is positioned intermediate the luminal graft member 184 and the abluminal graft member 182. The annular open region 187 is created by providing a plurality of microprojections 186 that project either radially inward from the luminal surface of the abluminal graft member 182 or radially outward from the abluminal surface of the luminal graft member 184. The plurality of microprojections 186 may also comprise a scaffold member interdisposed between the concentric graft members 184, 182. The plurality of microprojections 186 or scaffold member act as spacers which abut the opposing surface of either the luminal graft member 184 or the abluminal graft member 182 which bound the annular open region 187. The height of the microprojections 186 and, therefore, the size of the annular open region 187, are dimensioned such that cells may migrate through the annular open region 187, while blood flow or seepage will not occur between the lumen and the abluminal surface of the graft 180.

According to a specific aspect of the graft embodiment, the size of the plurality of openings in the luminal graft member 174, 184 may be different than the size of the plurality of openings in the abluminal graft member 172, 182. For example, the plurality of openings in the abluminal graft member 172, 182 preferably have a larger size than the plurality of openings in the luminal graft member 174, 184, while still retaining the out-of-phase relationship between the plurality of openings in the luminal 174, 184 and the abluminal 172, 182 graft members. Where circular openings are provided, it is preferable that the luminal 172, 182 and the abluminal 174, 184 graft members have openings having diameters of between about 5 µm and 100 µm.

Additionally, a third member may be interposed between the luminal 174, 184 and the abluminal 182, 172 graft members. The third member will preferably have a very fine plurality of openings, such as on the order of between 2-10 µm, and permits use of a higher porosity in the luminal and abluminal grafts, without the need to maintain an out-of-phase relationship between the openings in the luminal 174, 184 and the abluminal 172, 182 graft members.

The following examples are provided in order to illustrate the alternative embodiments of the invention, and are not intended to limit the scope of the invention.

EXAMPLE 1

Stent-Graft Formation

A self-expanding nickel-titanium stent was expanded and concentrically engaged about a 1.77 mm diameter copper substrate. The stent-substrate assembly was introduced into a sputter deposition chamber with a copper target. Copper was sputter deposited onto the stent-substrate assembly while the substrate was rotated. A negative voltage bias was applied. Deposition was allowed to run for about 4.5 hours to deposit a 300 µm thick film of copper. The deposition chamber was quenched with nitrogen.

The copper layer is planarized to expose the upper surfaces of the stent while leaving the copper layer present in interstices of the stent. The copper coated stent-substrate assembly was then introduced into a sputter deposition reactor and cleaned by glow discharge cleaning, a nickel-titanium target was employed to sputter deposit a 15 µm layer of NiTi onto the stent-substrate assembly during a 3.0 hour deposition run in the presence of a negative bias voltage. The reactor chamber was quenched with cold argon.

The NiTi coated stent-substrate was then placed into a nitric acid bath to selectively etch the copper substrate and the sacrificial copper from the stent and NiTi coating. It was found that the NiTi coating and the stent were well-adhered to each other.

EXAMPLE 2

Covered Stent Formation

A self-expanding nickel-titanium stent or a balloon expandable stainless steel stent having proximal and distal welding pad extensions is concentrically engaged onto a cylindrical copper substrate such that the outer diameter of the stent is between 5-10 µm less than the desired inner diameter of the cover to be deposited. The stent-substrate assembly is introduced into a sputter deposition reactor and copper is sputter deposited onto the stent-substrate assembly to a thickness at least equal to the thickness of the stent struts. The copper coated stent-substrate assembly is then removed from the sputter deposition reactor and mechanically polished such that the upper surfaces of the proximal and distal welding pad extensions are exposed, but a copper layer having a thickness between about 5-20 µm remains on the remainder of the stent and substrate. The assembly is then re-loaded into the sputter deposition reactor and back sputtered (such as by glow discharge) to remove oxide formed on the proximal and distal weld-pads, then NiTi is sputter deposited onto the assembly to a thickness of 4.5 µm covering the proximal and distal welding pad extensions of the stent, and the copper layer. A pattern of openings are formed through the NiTi film layer overlaying the copper film and those areas of the NiTi film overlaying the proximal and distal welding pad extensions. The assembly may then be introduced into a holding catheter and etched in a nitric acid etchant to remove the copper substrate and copper deposited layer.

EXAMPLE 3

Electrochemical Formation of Stent Patterned Substrate

A balloon expandable stainless steel stent was obtained and expanded to approximately a 3 mm inner diameter. Copper was plated onto the stent using a $H_2O/Cu_3(SO_4)_2$/glycerol solution with 1.5V applied for 30 seconds. The plating was burned and removed with a hot nitric acid solution. The surface was activated by applying −6.0V in the $H_2O/Cu_3(SO_4)_2$/glycerol solution. The plated stent was sonicated in water to remove copper dust. The plated stent was then plated for 20 min. at 1.3V in the same $H_2O/Cu_3(SO_4)_2$/glycerol solution. The copper layer was continuous over the surface of the stent, but flaked upon manual manipulation of the stent. The activation step was repeated for 5 seconds using 6.0V for cleaning and activation. The stent was left submerged in solution and plated at −1.0V for 10 seconds forming a very thin layer with improved adhesion to the stainless steel. The plated stent was capable of manual manipulation, crimping and re-expansion, with the adherent copper film remaining substantially continuous and adherent.

EXAMPLE 4

Method for Forming Monolithic Covered Stent

A tubular copper substrate was obtained. A negative imprint of a desired stent pattern was imparted onto the copper substrate either using the embossing die or a gravure calendaring roller having the desired stent pattern. The negative stent pattern is transferred onto the tubular copper substrate as a recessed pattern within the surface of the copper substrate by physically pressing the positive stent pattern onto the surface. Nitinol was then sputter deposited onto the copper substrate with the embossed stent pattern. After sputter deposition of the nitinol, the surface of the copper substrate plus deposited nitinol was planarized. The surface was subjected to glow discharge to clean the surface. A thin layer of nitinol was deposited onto the cleaned surface to form a thin film nitinol cover. The copper elements were chemically removed to release the stent with thin film nitinol cover. The stent and nitinol cover complex forming a substantially monolithic device.

EXAMPLE 5

Alternative Method for Forming Monolithic Covered Stent

A nitinol stent was fitted over a copper mandrel. A thin film of copper, approximately 300 µm in thickness, was deposited onto the copper mandrel fitted with the nitinol stent. The surface was planarized so that the nitinol stent was exposed and the surface was level, including surface between the nitinol and copper portions. The covered mandrel was subjected to glow discharge to clean the surface. After cleaning, a thin film nitinol cover was deposited onto the planarized and cleaned surface. The copper portions were removed, e.g., chemically etching copper, to result in a stent covered with a thin film nitinol cover. The overall structure has substantially monolithic characteristics.

EXAMPLE 6

Alternative Method for Forming Monolithic Covered Stent

A copper mandrel is obtained having a recessed stent pattern on its surface. A stent having the corresponding stent pattern is engaged into the recessed stent pattern in the mandrel so that the top surface of the stent is substantially coplanar with the non-recessed portions of the substrate's surface. The copper mandrel plus the fitted stent was subjected to glow discharge and the surface was cleaned. A continuous nitinol cover is vacuum deposited onto the stent and copper mandrel. The copper mandrel is removed by etching in a nitric acid etchant with the stent and formed NiTi film cover being adherent to the stent. The overall structure has substantially monolithic characteristics.

EXAMPLE 7

Method for Forming Stent having Multiple Microporous Covers

Iliac leg stent segments were glued to a ½ inch copper mandrel with ¼ inch adaptors at the ends covered with Kapton tape. The copper mandrel having circular grooves to index segments. Low Ap covers (20° C. to 30° C.) 2.9 µm diameter× 4.5 µm were expanded and slid over the stent segments, a second cover fitting over a first cover. The two covers used were 2147/S3 and 2152/S3, both having the pattern R505. The stent with two covers was welded with about 3000 welds throughout the whole surface of the stent. After welding the covers onto the stent, the combination was dipped in acetone to remove the glue. The copper parts were then etched away.

EXAMPLE 8

Alternative Method for Forming Stent Having Multiple Microporous Covers

Iliac leg stent segments were glued to a ½ inch copper mandrel with circular grooves to index segments. Low Ap covers (20° to 30° C.) 2.9 µm diameter×4.5 µm was expanded and slid over 22 mm section of the leg stent, while a ½ inch×7 µm R106 circumferential section, approximately 70 mm in length, was slid over the 12.7 mm leg stent section. A second cover was then expanded and slid over the first cover. The covers used were 2150/S3, 2148/S3 and 2166/S3. The stent with two covers was welded with about 3000 welds throughout the whole surface of the stent. After welding the covers onto the stent, the combination was dipped in acetone to remove the glue. The copper components were then etched in a nitric acid etchant.

While the invention has been described with reference to its preferred embodiments, those of ordinary skill in the relevant arts will understand and appreciate that the present invention is not limited to the recited preferred embodiments, but that various modifications in material selection, deposition methodology, manner of controlling the material heterogeneities of the deposited stent material, and deposition process parameters may be employed without departing from the invention, which is to be limited only by the claims appended hereto.

What is claimed is:

1. A method of making a medical device having a covered scaffold, comprising the steps of:
    a) Placing a deposition substrate on a pair of cylindrical rollers imparting a rotary movement to the deposition substrate along its longitudinal axis;
    b) Forming a pattern associated with the deposition substrate corresponding to a geometry for a scaffold;
    c) Forming the scaffold in association with the deposition substrate;
    d) Depositing a cover-forming material onto the formed scaffold, thereby monolithically joining the scaffold and the cover-forming material;
    e) Creating a plurality of openings passing through the cover-forming material; and
    f) Releasing the monolithically joined scaffold and cover-forming material from the deposition substrate.

2. The method of claim 1, wherein step b) further comprises the step of
    forming a pattern of recesses in the deposition substrate corresponding to a geometry for the scaffold; and
    wherein step c) further comprises the step of
    engaging a scaffold into the pattern of recesses in the deposition substrate.

3. The method of claim 2, wherein step b) further comprises a step of embossing the pattern of recesses in the deposition substrate.

4. The method of claim 2, wherein step b) further comprises a step of etching the pattern of recesses in the deposition substrate.

5. The method of claim 1, wherein step c) further comprises a step of disposing a scaffold onto the deposition substrate.

6. The method of claim 1, further comprising after step c) the steps of:
    i) depositing a sacrificial material onto the scaffold and the deposition substrate; and
    ii) planarizing the sacrificial material to expose the scaffold.

7. The method of claim 6, wherein step f) further comprises the step of removing the sacrificial material.

8. The method of claim 6, wherein step ii) further comprises the step of planarizing the sacrificial material to expose only at least one terminal end portion of the scaffold.

9. The method of claim 1, wherein steps c) and d) each further comprise the step of vacuum depositing the scaffold and cover-forming material, respectively.

10. The method of claim 1, wherein step d) further comprises the step of electrochemically depositing the cover-forming material.

11. The method of claim 1, after step d), further comprising the steps of:
    i) disposing a second scaffold member onto the cover-forming material;
    ii) depositing a sacrificial material onto the second scaffold member and the cover-forming material;
    iii) removing portions of the sacrificial material to expose portions of the second scaffold member; and
    iv) depositing a second cover-forming material onto the exposed portions of the second scaffold member and the sacrificial material.

12. The method of claim 11, wherein the step e) of creating a plurality of openings further comprises the step of creating a plurality of openings in the second cover-forming material, and step f) of releasing the monolithically joined scaffold and cover-forming material further comprises the step of removing the sacrificial material to form a void plenum between the cover-forming material and the second-cover forming material.

13. The method of claim 12, further comprising the step of loading at least one pharmacologically agent into the void plenum between the cover-forming material and the second cover-forming material.

14. A method of making a medical device having a covered scaffold, comprising the steps of:
   a) forming the scaffold in association with the deposition substrate;
   b) depositing a sacrificial material onto a scaffold-deposition substrate surface;
   c) planarizing the sacrificial material to expose the scaffold;
   d) depositing a cover-forming material onto the formed scaffold, thereby monolithically joining the scaffold and the cover-forming material;
   e) creating a plurality of openings passing through the cover-forming material; and
   f) releasing the monolithically joined scaffold and cover-forming material from the deposition substrate.

15. The method of claim 14, wherein step b) further comprises the step of vacuum depositing a sacrificial material onto the scaffold and substrate.

16. The method of claim 15, wherein step c) further comprises the step of planarizing portions of the sacrificial material to expose only terminal end portions of the scaffold.

17. The method of claim 16, wherein step f) further comprises the step of removing the sacrificial material.

18. The method of claim 1, wherein the cover forming material is a shape memory alloy having an austenite phase transition temperature is greater than 37° C.

19. The method of claim 1, wherein in step d) the cover forming material is sputter deposited onto the scaffold and substrate.

20. The method of claim 1, wherein a pharmaceutically active agent is loaded into the medical device, with a suitable carrier, excipient or matrix.

* * * * *